US005635379A

United States Patent [19]

Deghenghi

[11] Patent Number: 5,635,379
[45] Date of Patent: Jun. 3, 1997

[54] D-2-ALKYL-TRYPTOPHAN AND PEPTIDES CONTAINING SAME

[75] Inventor: Romano Deghenghi, Chesaux-Dessus, 1264-St. Cergue, Switzerland

[73] Assignee: Romano Deghenghi, St. Cergue, Switzerland

[21] Appl. No.: 550,046

[22] Filed: Oct. 30, 1995

Related U.S. Application Data

[60] Division of Ser. No. 16,862, Feb. 10, 1993, which is a continuation-in-part of Ser. No. 672,300, Mar. 20, 1991, abandoned.

[30] Foreign Application Priority Data

Nov. 5, 1990 [IT] Italy ........................ 20273-A

[51] Int. Cl.$^6$ ............. C12P 13/04; C12P 13/22; C12P 41/00
[52] U.S. Cl. ............ 435/106; 435/108; 435/227; 435/228; 435/280; 548/496; 548/497
[58] Field of Search ............... 435/106, 108, 435/227, 228, 280; 548/496, 497

[56] References Cited

U.S. PATENT DOCUMENTS

| | | | |
|---|---|---|---|
| 3,316,260 | 4/1967 | Shen et al. | 548/496 |
| 3,816,254 | 6/1974 | Chibata et al. | 435/280 |
| 3,907,638 | 9/1975 | Uzuki et al. | 435/280 |
| 4,256,641 | 3/1981 | Batcho et al. | 548/497 |
| 4,481,362 | 11/1984 | Nakai et al. | 435/280 |
| 4,497,957 | 2/1985 | Nakai et al. | 548/496 |
| 5,057,615 | 10/1991 | Kono et al. | 548/497 |
| 5,212,069 | 5/1993 | Kula et al. | 435/228 |

FOREIGN PATENT DOCUMENTS

| | | |
|---|---|---|
| 2016355 | 5/1990 | Canada. |
| 0 083 864 | 7/1983 | European Pat. Off.. |
| 0 203 031 | 11/1986 | European Pat. Off.. |
| 0 401 507 | 4/1990 | European Pat. Off.. |
| WO89/07110 | 8/1989 | WIPO. |

OTHER PUBLICATIONS

G. Tolis et al. "Growth Hormone Release in Thalassemic Patients by a New GH–Releasing Peptide Administered Intravenously or Orally". 75th Endocrine Society meeting, Las Vegas, NE, Jun. 9, 1993.
R. Deghenghi et al. "Structure–Activity Studies with Hexarelin and Related GH –Releasing Peptides" 3rd Intl. Pituitary Congress Marina de Rey, CA, Jun. 13–15, 1993.
E. Arvat et al. "GH–Releasing Activity of Hexarelin, A New Wynthetic Hexapeptide, After Intravenous, Subcutaneous, Intranasal and Oral Administration In Man" Giornate Endocrinologiche Pisane, Pisa (Italy) Jun. 28–29, 1993.

L.K. Conley et al, "Biological Potency of Hexarelin (EP23905)" Initial Studies on Oral Activity, presented 1992.
W. B. Wehrenberg et al, "Biological Potency of Hexarelin (EP23905), A New Growth Hormone–Releasing Peptide", presented 1992.
R. Deghenghi et al, "Hexarelin(EP23905)—A Superactive Growth Hormone Releasing Peptide", presented in Milan, Italy, Sep. 1992.
Paithorpe et al., Chemical Abstracts 79:400 (1973).
L.K. Conley et al, "Studies on the Mechanism of Action of Hexarelin and GHRP–6", presented at International Symposium on Growth Hormone II, Basic Clinical Aspects, in Tarpon Springs, Florida, Dec. 2–3, 1992.
B.P. Imbimbo et al, "Growth Hormone Releasing Activity of Hexarelin in Humans: A Dose–Responsive Study", presented at the International Symposium on Growth Hormone II, Basic Clinical Aspects, in Tarpon Springs, Florida, Dec. 3–6, 1992.
Silver et al., "Scleroderma, Fascitis, and Eosinophilia Associated With the Igestion of Tryptophan", The New England Journal of Medicine, 322: No. 13, (Mar. 29, 1990).
Karten et al., "Gonadotropin–Releasing Hormone Analog Design, Structure–Function Studies Toward the Development Agonists and Antagonists: Rationale and Perspective", Endocrine Reviews, 7(1):44–66 (1986).
Yabe et al., "Synthesis and Biological Activity of LH–RH Analogs Substituted by Alkyltryptophans at Postion 3", Chem Pharm. Bull., vol. 27 No. 8, (1979).
S. Majima, "E.W. Biologisches Verfahten der d–Tryptophandarstellans", Hoppe–Seyler's Z. Physiol Chem. 243–250 (1936).

*Primary Examiner*—Herbert J. Lilling
*Attorney, Agent, or Firm*—Pennie & Edmonds

[57] ABSTRACT

Peptides containing in its amino acid chain a D-2-alkylTryptophan residue wherein the alkyl group has between one and three carbon atoms and having pharmacological activity similar to that of analogous peptides containing natural unsubstituted D-Tryptophan residues in place of the D-2-alkylTryptophan. These new peptides are more resistant to oxidative degradation which usually takes place, for example, in the presence of reactive radicals or during high energy sterilization than unsubstituted Tryptophan containing peptides. Specific peptides include His-D-2-alkyl-Trp-Ala-Trp-D-Phe-Lys-$NH_2$, Ala-His-D-2-alkyl-Trp-Ala-Trp-D-Phe-Lys-$NH_2$, Pyro-Glu-His-Trp-Ser-Tyr-D-2-alkyl-Trp-Leu-Arg-Pro-Gly-$NH_2$, Pyro-Glu-His-Ser-Tyr-D-2-alkyl-Trp-Leu-Arg-Pro-$NHCH_2CH_3$, D-Pro-Gln-Gln-D-Trp-Phe-D-Trp-2-alkyl-Trp-Met-$NH_2$, Arg-D-Trp-N-methyl-Phe-D-2-alkyl-Trp-Leu-Met-$NH_2$, D-Phe-Cys-Phe-D-2-alkyl-Trp-Lys-Thr-Cys-$NHCH(CH_2OH)CHOHCH_3$ and D-Phe-Cys-Tyr-D-2-alkyl-Trp-Lys-Val-Cys-Trp-$NH_2$.

8 Claims, 20 Drawing Sheets

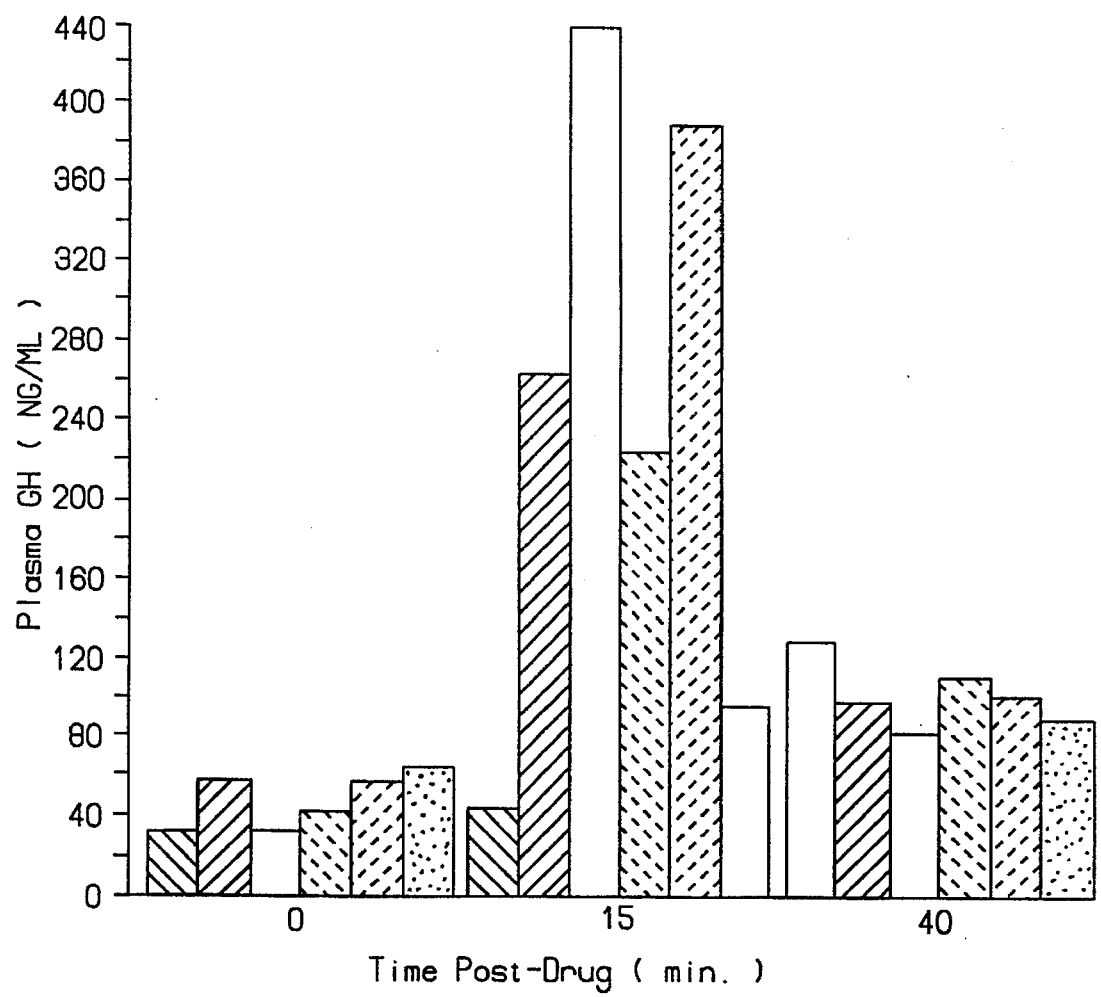
FIG. 11
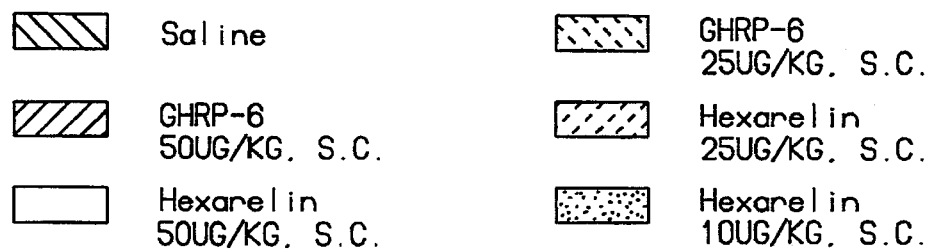

D-2-ALKYL-TRYPTOPHAN AND PEPTIDES CONTAINING SAME

CROSS REFERENCE TO RELATED APPLICATIONS

The present application is a divisional of Ser. No. 08/016,862 filed Feb. 10, 1993 which is continuation-in-part of application Ser. No. 07/672,300 filed Mar. 20, 1991 now abandoned.

TECHNICAL FIELD

The present invention relates to the field of biologically active peptides. Specifically, this invention relates to biologically active peptides containing the amino acid D-Tryptophan ("D-Trp").

BACKGROUND ART

It is well known that the incorporation or substitution of a D-Tryptophan residue into a biologically active peptide chain enhances the activity of that chain. Furthermore, such incorporation or substitution will prolong the biological activity. The prolonged and enhanced effectiveness of such peptides probably relates the increased resistance to degradation by peptidases.

Examples of D-Tryptophan containing peptides are the LHRH agonists as described by D. H. Coy et al., *Journal of Medical Chemistry*, volume 19, page 423 (1976), W. Koenig et al., *Peptide Chemistry* (1987), T. Shiba and S. Sakakibara (eds.), Osaka, *Protein Research Foundation*, Osaka (1988), page 591, B. J. A. Furr et al., *Journal of Endocrinol. Invest.*, volume 11, page 535 (1988). Examples of D-Tryptophan containing somastostatin analogs, such as the peptides octreotide and vapreotide are disclosed by R. Deghenghi, *Biomedicine and Pharmacotherapy*, volume 42, page 585 (1988). Another example of a D-Tryptophan containing peptide are the synthetic antagonists of Substance P as disclosed by D. Regoli et al., *European Journal of Pharmacology*, volume 99, page 193, (1984), and GHRP-6 described by C. Y. Bowers et al., *Endocrinology*, volume 114, page 1537, (1984).

Peptides containing Tryptophan have been subject to degradation due to the "Kynurenine pathway". In this pathway, the enzyme Tryptophan pyrrolase (i.e., indolamine 2,3-dioxygenase) degrades the pyrrole ring of Tryptophan. Kynurenine and other breakdown products are generated by this degradation. Some of the breakdown products have been shown to be toxic when present in elevated concentrations as reported by R. M. Silver et al., *The New England Journal of Medicine*, volume 322, page 874, (1990).

D-Tryptophan containing peptides are subject to degradation by oxygen and other reactive radicals as reported by R. Geiger and W. Koenig, "The Peptides," Academic Press, volume 3, page 82, New York (1981). The D-Tryptophan in the peptide chain may react with active or activated groups when peptides are formulated in certain controlled delivery pharmaceutical compositions, such as those based on polylactic/polyglycolic acid polymers. Such degradation is thought to be facilitated by either heat or by the presence of catalysts. It is also possible that radiolysis products formed during ionizing sterilization of these pharmaceutical compositions may facilitate the breakdown of D-Tryptophan. Clearly, the breakdown of D-Tryptophan, and the concomitant breakdown of the pharmaceutical compound containing D-Tryptophan is an undesirable effect.

Yabe et al., *Synthesis and Biological Activity of LHRH Analogs Substituted by Alkyl Tryptophans at Position 3*, Chem. Pharm. Bul. 27 (8) pp. 1907–1911 (1979) discloses seven analogs of LHRH in which the Tryptophan residue at position 3 was replaced by various L-methyl Tryptophans and L-ethyl Tryptophans. However, each analog tested exhibited reduced hormonal activity compared to synthetic LHRH.

What is needed is a derivative of D-Tryptophan which retains the prolonged and increased biological activity discussed above, while resisting degradation by indolamine dioxygenase, oxygen or other reactive radicals. It is of course essential that such a derivative of D-Tryptophan would maintain biological activity as compared to D-Tryptophan containing bioactive peptides.

The terms "biological effect" or "pharmacological effect" as used in the present disclosure refer to the qualitative effect that a bioactive peptide has upon living tissue. As an example, LHRH, luteinizing hormone releasing hormone, has the biological effect of causing cells of the anterior pituitary gland to release luteinizing hormone. In contrast, the term "potency" is used in its conventional sense to refer to the degree and duration of the bioactivity of a given peptide.

Utilizing these terms as defined above, what is needed is a Tryptophan containing bioactive peptide which is resistant to oxidative degradation and reactive radical attack while maintaining the same biological activity and a similar or greater potency than the presently available analogous peptides provide.

SUMMARY OF THE INVENTION

Now in accordance with the present invention, a derivative of D-Tryptophan has been discovered which imparts to a biologically active peptides incorporating that derivative improved resistance to the oxidative breakdown reaction of Tryptophan, while maintaining the biological activity and pharmacological effect exhibited by peptides incorporating unaltered D-Tryptophan.

Specifically, the present invention relates to a Tryptophan derivative, namely D-2-alkyl-Tryptophan, in which the alkyl substituent in the 2 position is a lower alkyl group, preferably one containing 1 to 3 carbon atoms. Peptides incorporating such substituted D-Tryptophans are more stable in the presence of reactive radicals or when pharmaceuticals containing such peptides are exposed to ionizing radiation.

This invention also describes a more practical synthesis of D-2-Methyl Tryptophan and the preparation of novel protected D-2-Methyl Tryptophan derivatives particularly suited for use in the synthesis of peptides.

A particularly preferred peptide containing this modified Tryptophan derivative is an analog of GHRP (Growth Hormone Releasing Peptide), His-D-2-alkyl-Trp-Ala-Trp-D-Phe-Lys-$NH_2$, which is referred to in the trade as HEXARELIN.

The invention also relates to a new method for preparing D-2-alkyl-Tryptophan which comprises treating a solution of racemic $N^\alpha$-acetyl-2-alkyl-Tryptophan with acylase for a sufficient time and at a sufficient temperature to form insoluble material therein, recovering and lyophilizing the insoluble fraction to form a residue, dissolving the residue in a suitable solvent, subjecting the solvent and dissolved residue to chromatography to obtain highly polar fractions and lesser polar fractions, collecting the lesser polar fractions to obtain a $N^\alpha$-acetyl-D-2-alkyl-Tryptophan compound and hydrolyzing the thusly obtained compound to obtain D-2-alkyl-Tryptophan.

In this method, the racemic $N\alpha$-acetyl-2-alkyl-Tryptophan is treated by dissolution in water with a base, such as potassium hydroxide, and retaining the solution for about 24 hours at about 40° C. The $N^\alpha$-acetyl-D-2-alkyl-Tryptophan is then hydrolyzed under an inert gas, such as nitrogen, with a base, such as KOH or NaOH, for about 24 hours at 100° F., prior to the addition of an acid, such as acetic acid, and the cooling of the solution. Also, the insoluble fraction can be obtained by filtration and the residue may be formed by lyophilizing the insoluble fraction to dryness. It is preferred for the residue to be dissolved in the upper phase of N-BaOH-AcOH-H$_2$O before being introduced into the chromatography column.

BRIEF DESCRIPTION OF THE DRAWINGS

FIGS. 6, 7, 8, 9, 10 and 11 are graphical representations of GH release in anesthetized male rats following subcutaneous administration of saline, GHRP-6 and HEXARELIN;

DETAILED DESCRIPTION OF THE INVENTION

Figure 1:
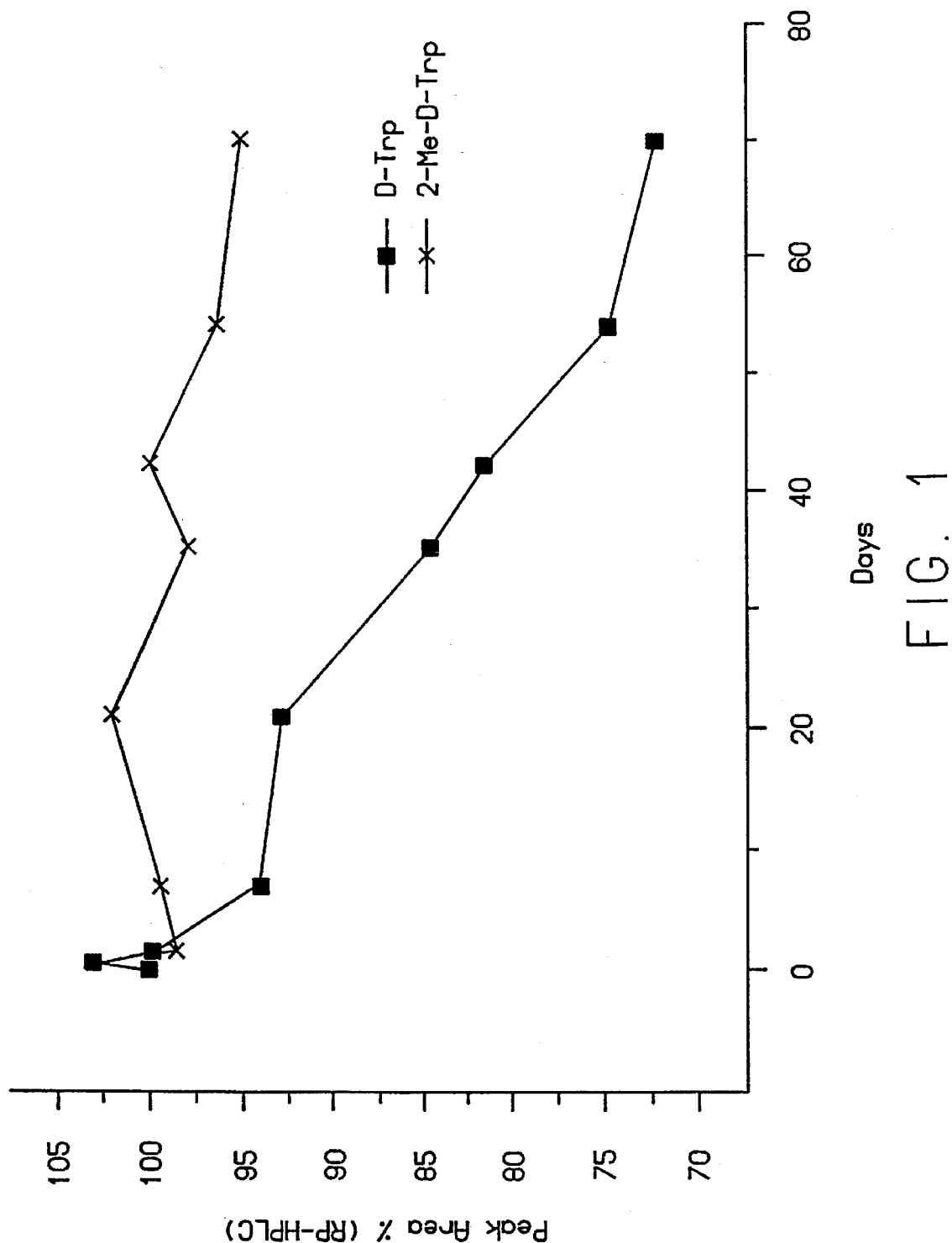
FIG. 1 is a graphical representation of the stability of D-Trp and D-2-methyl-Trp in an acid solution.

Biologically active peptides in accordance with the present invention include:

His-D-2-alkyl-Trp-Ala-Trp-D-Phe-Lys-NH$_2$,
Ala-His-D-2-alkyl-Trp-Ala-Trp-D-Phe-Lys-NH$_2$,
Pyro-Glu-His-Trp-Ser-Tyr-D-2-alkyl-Trp-Leu-Arg-Pro-Gly-NH$_2$,
Pyro-Glu-His-Ser-Tyr-D-2-alkyl-Trp-Leu-Arg-Pro-NHCH$_2$CH$_3$,
D-Pro-Gln-Gln-D-Trp-Phe-D-Trp-2-alkyl-Trp-Met-NH$_2$,
Arg-D-Trp-N-methyl-Phe-D-2-alkyl-Trp-Leu-Met-NH$_2$,
D-Phe-Cys-Phe-D-2-alkyl-Trp-Lys-Thr-Cys-NHCH(CH$_2$OH)CHOHCH$_3$
and D-Phe-Cys-Tyr-D-2-alkyl-Trp-Lys-Val-Cys-Trp-NH$_2$
where alkyl designates a lower alkyl group, preferably comprising 1 to 3 carbons. The methyl group is most preferred due to simplicity of manufacture.

The first peptide, named HEXARELIN, is an analog of GHRP and is used for stimulating the release of growth hormone. The second peptide is an analog of the first and contains one additional amino acid.

The third and fourth peptides listed above are analogs of the natural peptide Pyro-Glu-His-Trp-Ser-Tyr-Trp-Leu-Arg-Pro-Gly-NH$_2$ (SEQ ID NO:1), which is a luteinizing hormone releasing hormone (LH-RH), i.e., a neurohumoral hormone produced in the hypothalamus which stimulates the secretion of the LH luteinizing hormone by the anterior pituitary gland. These peptides pertain therefore to the class of LHRH agonists and are also defined respectively as follows: [D-2-methyl-Trp$^6$]LHRH and [Des-Gly$^{10}$-D-2-methyl-Trp$^6$-Pro-ethylamide$^9$]LHRH.

The fifth and sixth peptides listed above are antagonists of substance P. Substance P is a neurotransmitter used by sensory neurons that convey responses of pain or other noxious stimuli to the central nervous system. Accordingly, these peptides have analgesic and anti-inflammatory effects.

The seventh and eighth peptides are analogs (agonists) of somatostatin and as such show antisecretory and antitumoral activity.

Although the aforementioned examples of the present invention disclose specific embodiments thereof, it is believed that the substitution of an D-2-alkylTryptophan in bioactive peptide containing at least one Tryptophan residue will yield bioactive peptides providing the advantages and benefits discussed above.

The incorporation of a D-2-alkylTryptophan in bioactive peptides as described above provides a method for prolonging and preserving the activity of such peptides. When analogous bioactive peptides not substituted with an D-2-alkylTryptophan are exposed to various processing conditions and substances, the activity of such peptides may be adversely effected. Sterilizing procedures used in the pharmaceutical industry may expose bioactive compounds to ionizing radiation. Such radiation may effect the formation of reactive radicals. Tryptophan containing peptides are particularly susceptible to attack by such radicals and such attack may render the peptide ineffective, or possibly toxic. Furthermore, various formulating compounds, such as polylactic-polyglycolic acid polymers may contain active, or activated groups which may also attack Tryptophan containing bioactive peptides. The present invention provides a method for protecting a tryptophan containing bioactive peptide from these manufacturing hazards while also increasing the peptides resistance to oxidative degradation after formulation is complete. It is believed that the presence of the alkyl group at the number 2 position of the Tryptophan increases the stability of the pyrrole ring wherein attack by reactive radicals and active or activated groups occurs.

2-methyl-Tryptophan is known (cf. H. N. Rydon, J. Chem. Soc. 1948, 705) and the homologous alkylated derivatives are conveniently prepared from the corresponding 2-alkyl indoles by well known methods (cf. J. P. Li et al., *Synthesis* (1), 73, 1988). The resolution of the racemic Tryptophan derivatives to give the D-enantiomers of the present invention can be achieved by a variety of methods (cf. Amino Acids, Peptides and Proteins, Vol. 16, pages 18–20, The Royal Society of Chemistry, London, 1985). Specifically, S. Majima (Hoppe-Seyler's Z. Physiol. Chem. 243, 250 (1936) describes the digestion of 2-Methyl Trp with colibacteria with isolation of the undigested D-isomer. A more practical synthesis of D-2-Methyl Trp is given in Example 1. Both the solution phase or the solid phase method of peptide synthesis can be used to make the peptides of this invention. (cf. R. Geiger et al., "The Peptides", Academic Press, New York 1981). If the solid phase method is used, peptide synthesizers such as the Applied Biosystem 430A, Bioresearch Sam 9500 or the Beckman Model 990 are preferably used.

According to this methodology, the first amino acid is linked to the benzhydrylamine resin and the remaining protected amino acids are then coupled in a step wise manner using the standard procedures recommended by the manufacturers of the synthesizers. For instance, amino acid couplings are performed by using symmetrical anhydrides in the Applied Biosystems Synthesizer and diisopropylcarbodiimide in the Bioresearch or Beckman machines. The amino acid derivatives are protected by the tertiary butoxycarbonyl groups or by Fmoc (9-Fluorenyl methoxycarbonyl) groups on the alpha-amino function during the synthesis. The functional groups present in the amino-acid in the side chain are previously protected, e.g. by acetyl(Ac), benzoyl (Bz), t-butyloxycarbonyl (Boc), benzyloxymethyl (Bom), benzyl (Bzl), benzyloxycarbonyl (Z), formyl (For), p-nitrophenyl ester (ONp), tosyl (Tos), etc. For instance, the functional groups of Histidine are protected by benzyloxymethyl (His(Bom)), tosyl (His(Tos)), the functional groups of Tryptophan by formyl (Trp(For)), those of Serine by benzyl (Ser(Bzl)), those of Tyrosine by 2-Br-benzyloxycarbonyl (Tyr(2-Br-Z)), those of Arginine by tosyl (Arg(Tos)), those of Leucine by O-benzyl-p-tosyl (Leu(O-Bzl-p-Tos)), those of Proline by O-benzyl HCl (Pro(O-Bzl HCl)), those of Glycine by O-benzyl HCl (Gly (O-Bzl HCl)), those of Cysteine by 4-methyl-benzyl (Cys(4-Me-Bzl)), those of Lysine by benzyloxycarbonyl (Lys(Z)), those of Threonine by benzyl-OH (Thr(Bzl-OH)), those of Valine by O-benzyl-tosyl (Val(O-Bzl-p-Tos)), those of Glutamic Acid by O-benzyl (Glu(O-Bzl)), those of Methionine by P-nitrophenyl ester (Me(Onp)), and those of Alanine by O-benzyl HCl (Ala(O-Bzl HCl).

The Boc protective groups on the alpha-aminic function are removed at each stage by treatment with 60% trifluoroacetic acid ("TFA") in dichloromethane. Cleavage of Trp and Met containing peptides from the resin with simultaneous removal of all side-chain protecting groups is achieved as described by J. P. Tam et al., *J. Am. Chem. Soc.*, Vol 105, page 6442 (1983). The crude peptides after HF cleavage are purified on a Sephadex G-50 F column in 50% acetic acid or by preparative reverse phase HPLC using gradients of acetonitrile and water containing 0.1% trifluoroacetic acid.

EXAMPLES

The examples that follow are given for illustrative purposes only, but are not limitative of the present invention.

Example 1

Synthesis of D-2-Methyl-Tryptophan $N^\alpha$-Acetyl-2-methyl-D,L-tryptophan [Y. Yabe et al. Chem. Pharm. Bull. 27(8) 1907–1911 (1979)] 1.3 g (5 mmol), was suspended in 50 ml of water and dissolved by adding concentrated ammonium hydroxide to a pH of 7.5. 5 mg of acylase (from porcine kidney, Sigma Grade III lyophilized) was added and the mixture kept at 40° C. for 24 hours. The insoluble material was separated by filtration and the filtrate was lyophilized to dryness. The residue was dissolved in the upper phase (10 ml) of n-BuOH-AcOH-$H_2O$ (16:1:20) and chromatographed on a 3.5×50 cm column of Sephadex G-25 (Pharmacia, Fluka) collecting 10 ml fractions. The less polar fractions (N° 16–25) were pooled to give mainly undigested $N^\alpha$-acetyl-2-methyl-D-tryptophan which, without purification, was hydrolized under $N_2$ with a solution of 1 g KOH in 25 ml of water at 100° F. for 24 hours. Acetic acid (2 ml) and water (10 ml) were added to the hot solution and placed in the refrigerator for 12 hours. The crude resulting 2-methyl-D-tryptophan was filtered, washed and dried and recrystallized from hot water (charcoal) to yield the title compound, m.p. 244°–246°, $[\alpha]_D^{20}$+18.6, [c0.26($H_2O$)].

Figure 2:
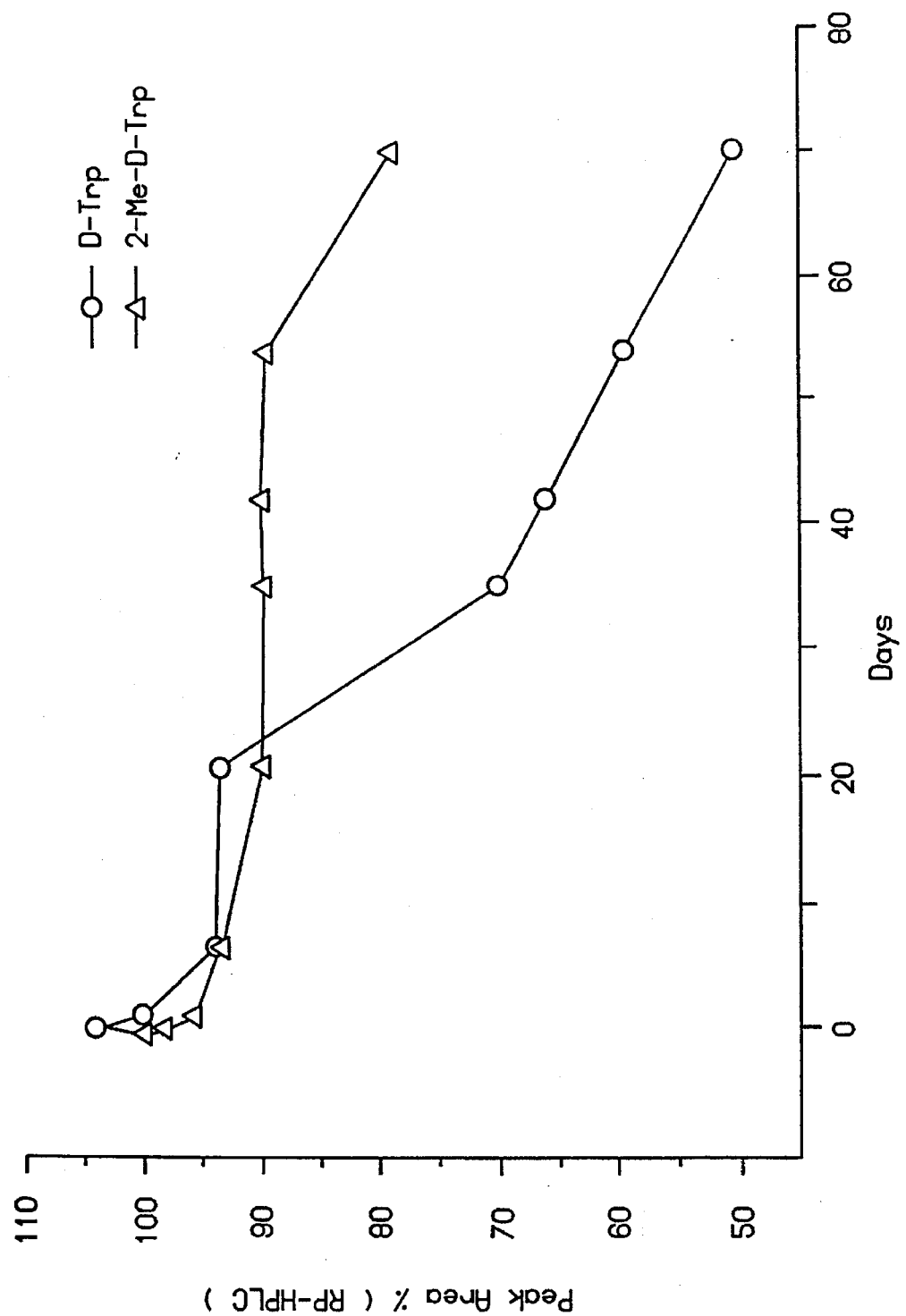
FIG. 2 is a graphical representation of the oxidative degradation of D-Trp and D-2-methyl-Trp in solution.

The enhanced stability of the 2-methyl-Tryptophan derivative is illustrated in FIGS. 1 and 2. In FIG. 1, the stability of this derivative is compared to D-Trp for 1% solutions at a pH of 2.2 (0.2M citrate buffer with 0.02% $NaN_3$ added) which are maintained in the dark under helium, while FIG. 2 shows the oxidative degradation of these compounds in 1% solutions at a pH of 5.4 (0.2M acetate buffer with 0.02% $NaN_3$ added) under oxygen and constant light. The peak area is measured by HPLC. The results show that the substituted Trp is stable for 60 days or longer, whereas the unsubstituted Trp began to lose stability after about 20 days.

Example 1a

Synthesis of Fmoc-D-2-Methyl-Trp $N^\alpha$-[9 Fluorenylmethyloxycarbonyl]-2-methyl-D-Tryptophan (Fmoc Derivative)

To a suspension of 436 mg of 2-methyl-D-Tryptophan of Example 1 (2 mMole) in 5 ml of water, a solution of 710 mg (2.1 mMole) of Fmoc-OSu (9 FluorenylmethyloxyN-hydroxysuccinimide) in 2 ml of dioxane is added dropwise and the mixture is stirred overnight at room temperature. The mixture is extracted with ether and the ether phase discarded. The aqueous phase is adjusted to pH 1 with 6N HCl and extracted with ethylacetate. The organic phase is washed with water, dried over $Na_2SO_4$ and evaporated in vacuo. The residue is dissolved in ether and hexane is added to precipitate the chrystalline product which is filtered and dried.

M.p. 196°–198° C. TLC: Rf 0.45 in $CHCl_3$/MeOH/AcOH 85/10/5

|  | C | H | N |
|---|---|---|---|
| Calculated | 73.62% | 5.49% | 6.36% |
| Found: | 73.72% | 5.29% | 6.27% |

Additional suitably protected 2-Methyl-D-Tryptophans have the formula:

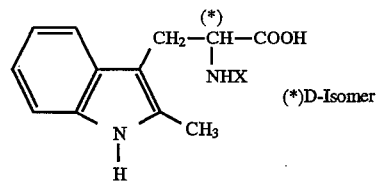

(*)D-Isomer

Where X is BZ (Benzoyl) or Z (Benzyloxycarbonyl). These can be prepared by conventional methods, starting from the 2-Methyl-D-Tryptophan.

Examples 2–9

Peptides which include the D-2-methyl Trp were made as follows:

Example 2

Pyro-Glu-His-Trp-Ser-Tyr-D-2-alkyl-Trp-Leu-Arg-Pro-Gly-$NH_2$

The protective groups for the side chains are Tosyl (Tos) for Arginine and Histidine and Bromo-benzyloxycarbonyl (2-Br-Z) for Tyrosine. The benzhydrylamine resin (2.2 g) (Bachem®), was cross-linked at 1% with Proline and the apparatus used was a Beckman Model 990. The amino acids protected by Boc (tert-butyloxycarbonyl) are coupled with dicyclohexylcarbodiimide. The Boc groups are removed by trifluoroacetic acid in methylene chloride.

The synthesis yielded 4.07 g of the decapeptide-resin (98% of theoretical weight gain). Part of this resin (1.5 g) was stirred at 0° centigrade for 30 minutes with HF (24 ml) and anisole (8 ml). HF was then removed as rapidly as possible (ca. 60 min) in vacuo and EtOAc was added to the thus obtained residue. Solid material was filtered, washed with EtOAc, dried, and extracted with 2M AcOH. Lyophilization gave a white powder which was purified by gel filtration on a column (2.5×95 cm) of Sephadex G-25 (fine) by elution with 2M AcOH. The eluate portion corresponding to the major peak was then dried and eluted further on a column (2.5×95 cm) of Sephadex G-25 (fine) previously equilibrated with the lower phase followed by the upper phase of the following biphasic solvent mixture n-BuOH-AcOH-$H_2O$ (4:1:5). Elution with the upper phase gave a major peak and the peptide from this area was collected, concentrated to dryness, and lyophilized from dilute AcOH to give the titled peptide as a white powder. Amino acid analysis was consistent with the desired structure.

Example 3

Pyro-Glu-His-Ser-Tyr-D-2-alkyl-Trp-Leu-Arg-Pro-NHCH$_2$CH$_3$

The peptide was assembled on a 1% cross-linked Pro-Merrifield resin (2.0 g, 1.0 mmol of Pro) using the same conditions and protecting groups employed in Example 1, with the exception that dinitrophenol group protection was used for the imidazole group of histidine. The peptide-resin obtained (3.45 g) was stirred with ethylamine (20 ml, 0° C.) for 6 hours and excess amine was removed in vacuo. The protected peptide resin was extracted with MeOH and precipitated by the addition of a large excess of EtOAc to give 1.36 g of material. The obtained product was treated and deprotected with HF-anisole and crude peptide obtained after this treatment was purified by gel filtration followed by partition chromatography to yield the homogeneous peptide cited. Amino acid analysis was consistent with the desired structure.

Examples 4–9

Using the above described methods with appropriate modifications well known to the skilled in the art particularly the use of Fmoc derivatives as protected amino acids of Example 1a for the preparation of Fmoc-D-2 Methyl Trp or other suitably protected amino acids, the following peptides are synthesized:

Example 4

His-D-2-alkyl-Trp-Ala-Trp-D-Phe-Lys-NH$_2$ ("HEXARELIN"),

Example 5

Ala-His-D-2-alkyl-Trp-Ala-Trp-D-Phe-Lys-NH$_2$,

Example 6

D-Pro-Gln-Gln-D-Trp-Phe-D-Trp-2-alkyl-Trp-Met-NH$_2$,

Example 7

Arg-D-Trp-N-methyl-Phe-D-2-alkyl-Trp-Leu-Met-NH$_2$,

Example 8

D-Phe-Cys-Phe-D-2-alkyl-Trp-Lys-Thr-Cys-NHCH(CH$_2$OH)CHOHCH$_3$ and

Example 9

D-Phe-Cys-Tyr-D-2-alkyl-Trp-Lys-Val-Cys-Trp-NH$_2$

The peptides of Examples 4 and 5 were tested as Growth Hormone releasers in rats. GH released in a series of seven 10-day old rats, injected subcutaneously with a standard dose of 160 μg/kg and sacrificed 15 minutes after the injection. Results are as follows:

| Samples | GH (ng/kg) |
| --- | --- |
| Untreated Controls | 14.64 + 21.41 |
| Example 4 | 201.00 + 39.55 |
| Example 5 | 212.00 + 48.63 |

Thus, the peptides of Examples 4 and 5 (i.e., His-D-2-methyl-Trp-Ala-Trp-D-Phe-Lys-NH$_2$ and Ala-His-D-2-methyl-Trp-Ala-Trp-D-Phe-Lys-NH$_2$) were found to be very active analogs.

Example 10

The peptide of Example 4 (i.e., HEXARELIN) was compared with GHRP-6 {Bowers C. Y., Momany F. A., Reynolds G. A., and Hong A. (1984) On the in Vitro and in Vivo Activity of a New Synthetic Hexapeptide that Acts on the Pituitary to Specifically Release Growth Hormone, Endocrinology, 114: 1537–1545} both in vitro and in vivo, as follows.

Male Sprague Dawley rats (Charles River, Calco, Italy) of 2–3 months of age were used. Rats were housed at 22 +2° C., with lighting cycle of 14 h light: 10 h dark (lights on from 06.00 to 20.00 h), at least 10 days before starting the experiments. A standard dry diet and water were available ad libitum.

In Vitro Experiments: Pituitary Cell Culture

Pituitary tissue used for cell dissociation included only the anterior lobe. Briefly, pituitary glands were collected in sterile F-10 medium and after cutting into small fragments incubated twice (30 minutes each) at 37° C. in F-10 medium containing 6% fetal calf serum and collagenase (2.5 mg/ml) (Boehringer, Mannheim GmbH, Germany). Fragments were then washed in Dulbecco's PBS, $Ca^{2+}$ and $Mg^{2+}$ free medium and mechanically dissociated. Single cell suspension was planted onto 24-well (2×10$^5$ cells/well) culture plates. The cells were incubated in F-10 medium supplemented with 10% horse serum, 4% fetal calf serum and gentamycin (25 μg/ml), in a humidified atmosphere of 5% $CO_2$ and 95% air at 37° C.

After 3 days, the medium was removed and the cells washed twice with serum free F-10, then incubated with 1 ml of F-10 containing 0.1% BSA only, or with added various concentrations of synthetic peptides.

After incubation for 2 h at 37° C., media were collected and stored frozen at −20° C. until assayed for measurement of GH content.

In Vivo Experiments: Experimental Procedure

Between 09.00–10.00 h rats were anesthetized with ketamine (58 mg/kg, Inoketam, VIRBAC, Milano) and xilazine (12 mg/kg, Rompun, Bayer, Milano). Thirty minutes later, a blood sample (250 μg) was withdrawn from the exposed jugular vein, peptides were injected intravenously or subcutaneously, and further blood samples were collected 10, 20 and 30 minutes later.

Medium and plasma GH was measured by radioimmunoassay using materials supplied by the NIADDK Bethesda, Md. Values were expressed in term of NIASSK-rat-GH-RP-2 standard (potency 2 IU/ml), as ng/ml of medium or plasma.

The minimum detectable value of rat was 1.0 ng/ml; intra-assay variability was 6%. To avoid inter-assay variation, samples from each experiment were assayed simultaneously. The results were as follows:

In Vitro Experiments

When pituitary cell monolayers were incubated for two hours with increasing concentrations ($10^{-8}$ to $10^{-6}$M) of HEXARELIN and GHRP-6, stimulation of GH secretion over basal secretion was observed. Comparison of the GH secretion levels obtained after stimulation of pituitary cell monolayers with GHRP-6 and HEXARELIN indicates that their activities were very similar, as shown in Table 1.

Figure 3:
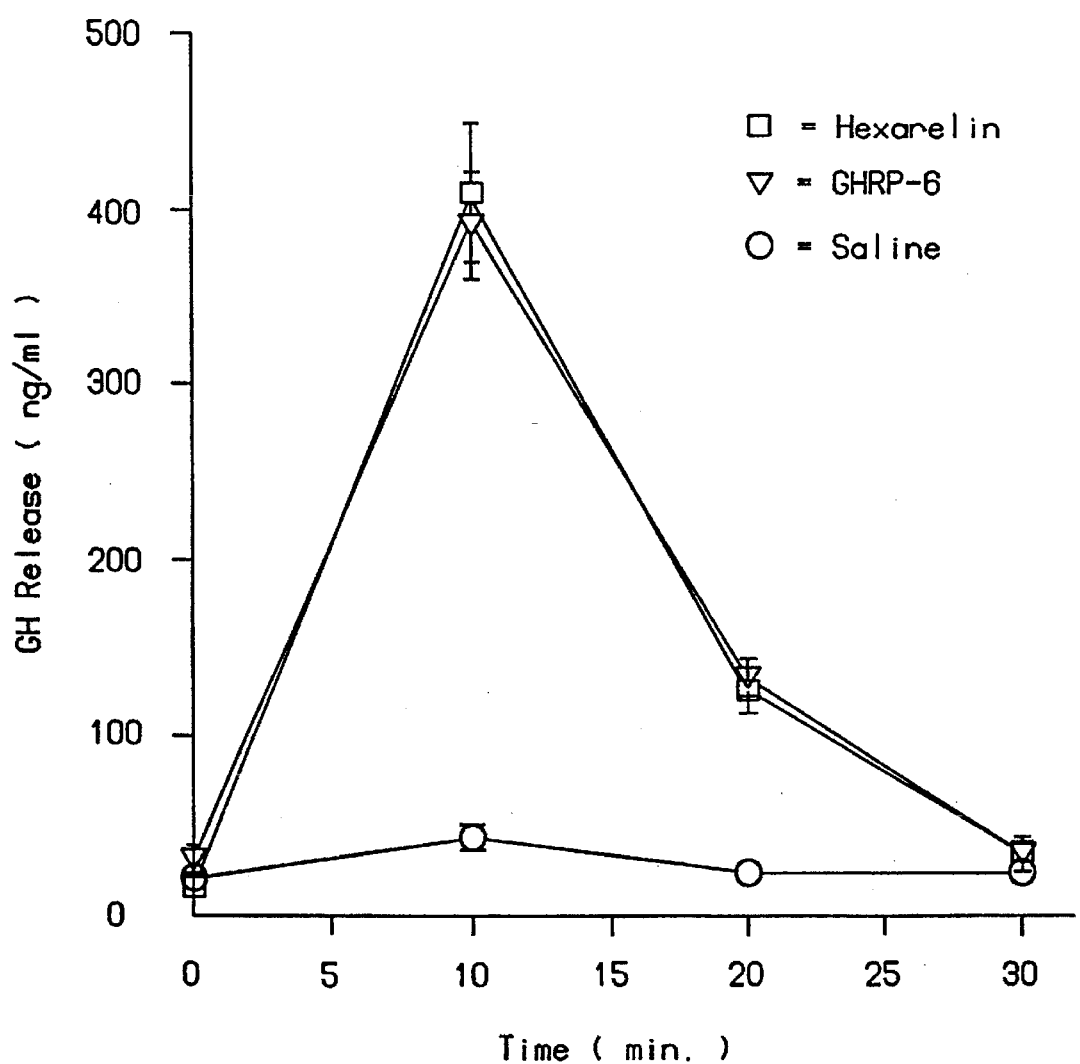
FIGS. 3, 4 and 5 are graphical representations of GH release in anesthetized male rats following intravenous administration of saline, GHRP-6 and HEXARELIN.
Figure 4:
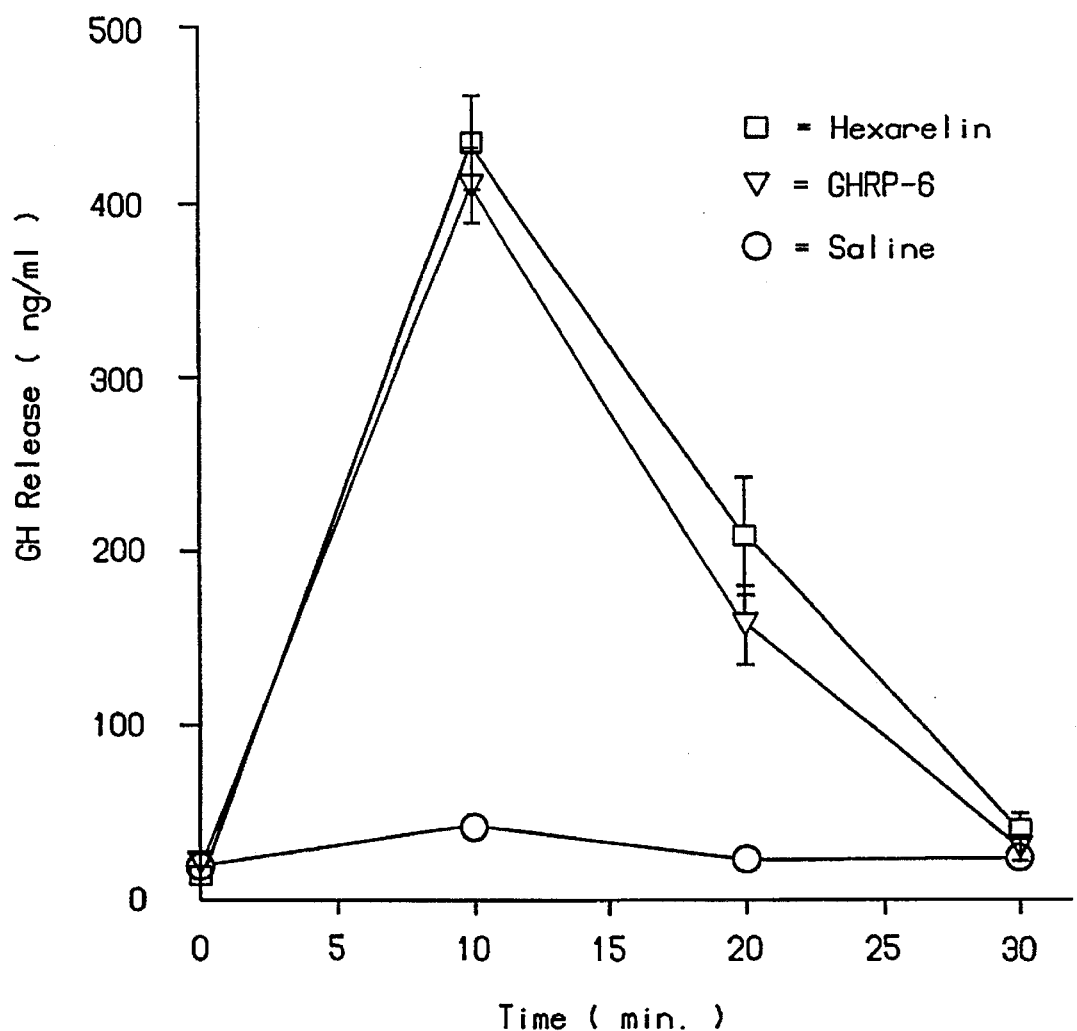
Figure 5:
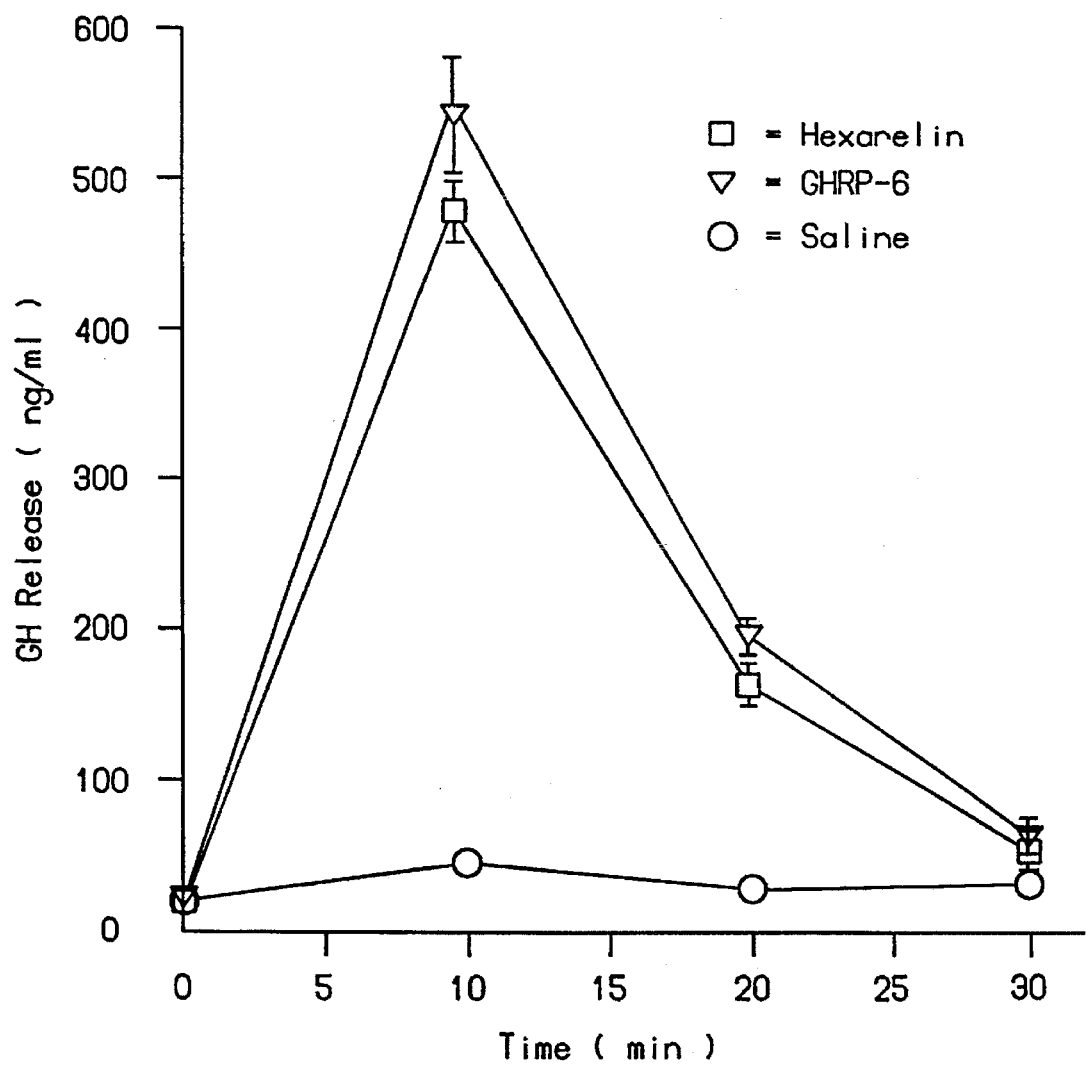

These data are also illustrated in FIGS. 3-5.

Potency and time-course of the effects of the two peptides were almost superimposable. In anesthetized rats, subcutaneous administration of HEXARELIN (150, 300 and 600 µg/kg) elicited a significant increase in plasma GH concentrations 10, 20 and 30 minutes after treatment. A similar profile of secretion was obtained after the administration of GHRP-6 at the same dose levels, as shown in Table 3. In this instance HEXARELIN appeared more effective than GHRP-6 at all the considered times. In all, both peptides after subcutaneous administration elicited a more prolonged stimulation of GH secretion although the maximum peak levels were considerably lower than those reported after intravenous injection.

TABLE 1

GH-RELEASING ACTIVITY OF GHRP-6 AND HEXARELIN

| TREATMENT | CONCENTRATION (M) | | | |
|---|---|---|---|---|
| | 0 | $10^{-8}$ | $10^{-7}$ | $10^{-6}$ |
| GHRP-6 | 484.2 ± 11.4 | 544.2 ± 23.9 | 526.5 ± 19.0 | 510.0 ± 12.0 |
| HEXARELIN | 471.1 ± 31.3 | 557.8 ± 15.9 | 589.1 ± 17.9 | 558.0 ± 19.1 |

Pool of controls 492.5 ± 12.4 GH (ng/well)
Values (ng/well) are the means + S.E.M. of 6 determinations per group.
Pituitary cell monolayers were incubated with peptides for 2 hours.

In Vivo Experiments

In anesthetized rats the administration of graded doses (150, 300 and 600/µg/kg) of HEXARELIN elicited significant increases of plasma GH concentrations 10 and 20 minutes after administration. Similar results were obtained after injection of the same doses of GHRP-6, as shown in Table 2.

TABLE 2

COMPARISON OF THE GH-RELEASING ACTIVITY OF
GHRP-6 (A) AND HEXARELIN (B) ADMINISTERED I.V. IN
MALE RATS ANESTHETIZED WITH KETAMINE AND XILAZINE

| TREATMENT | TIME (minutes) | | | |
|---|---|---|---|---|
| | 0 | 10 | 20 | 30 |
| Control | 19.8 ± 5.8(8) | 45.6 ± 7.5(8) | 28.7 ± 4.8 | 32.2 ± 4.5(4) |
| A 150 µg/kg | 30.2 ± 7.8(7) | 394.0 ± 31.0(7) | 139.3 ± 10.2(7) | 42.5 ± 4.5(4) |
| B 150 µg/kg | 15.0 ± 2.9(8) | 412.7 ± 39.7(8) | 132.2 ± 12.7(8) | 44.0 ± 6.0(4) |
| A 300 µg/kg | 21.9 ± 4.4(8) | 413.6 ± 21.5(8) | 162.7 ± 22.1(8) | 38.2 ± 7.7(4) |
| B 300 µg/kg | 13.5 ± 2.0(7) | 438.5 ± 26.8(7) | 213.8 ± 34.2(7) | 48.1 ± 8.8(3) |
| A 600 µg/kg | 21.2 ± 6.1(8) | 542.0 ± 38.0(8) | 195.5 ± 11.0(8) | 64/0 ± 11.9(4) |
| B 600 µg/kg | 18.4 ± 4.3(8) | 478.3 ± 19.8(8) | 164.2 ± 13.2(8) | 54.5 ± 13.3(4) |

Values (ng/ml) are means ± S.E.M.
Number of rats are shown in parentheses and refer to pooled data of 2-3 experiments in which similar data were obtained.

TABLE 3

COMPARISON OF THE GH-RELEASING ACTIVITY OF
GHRP-6 (A) AND HEXARELIN (B) ADMINISTERED S.C.
IN MALE RATS ANESTHETIZED WITH KETAMINE AND XILAZINE

| TREATMENT | TIME (minutes) | | | |
|---|---|---|---|---|
| | 0 | 10 | 20 | 30 |
| Control | 26.0 ± 8.0(11) | 22.0 ± 3.3(8) | 59.2 ± 8.1(11) | 52.2 + 5.5(11) |
| A 150 µg/kg | 20.0 ± 5.0(8) | 63.1 ± 11.0(8) | 110.4 ± 18.0(8) | 77.2 ± 14.0(8) |
| B 150 µg/kg | 12.0 ± 4.0(7) | 107.1 ± 17.7(7) | 156.6 ± 18.7(7) | 86.0 ± 18.9(7) |
| A 300 µg/kg | 20.0 ± 6.0(8) | 63.9 ± 12.8(8) | 123.4 ± 14.6(8) | 87.7 ± 11.8(8) |
| B 300 µg/kg | 12.0 ± 4.0(7) | 80.6 ± 11.0(7) | 171.7 ± 22.0(7) | 102.7 ± 17.0(7) |
| A 600 µg/kg | 18.0 ± 4.0(10) | 93.1 ± 22.3(7) | 167.1 ± 14.7(10) | 107.8 ± 9.5(10) |
| B 600 µg/kg | 23.0 ± 6.0(10) | 90.7 ± 16.6(7) | 187.5 ± 15.4(10) | 115.3 + 19.1(10) |

Values (ng/ml) are means ± S.E.M.
Number of rats are shown in parentheses and refer to pooled data of 2–3 experiments in which similar data were obtained.

Figure 6:
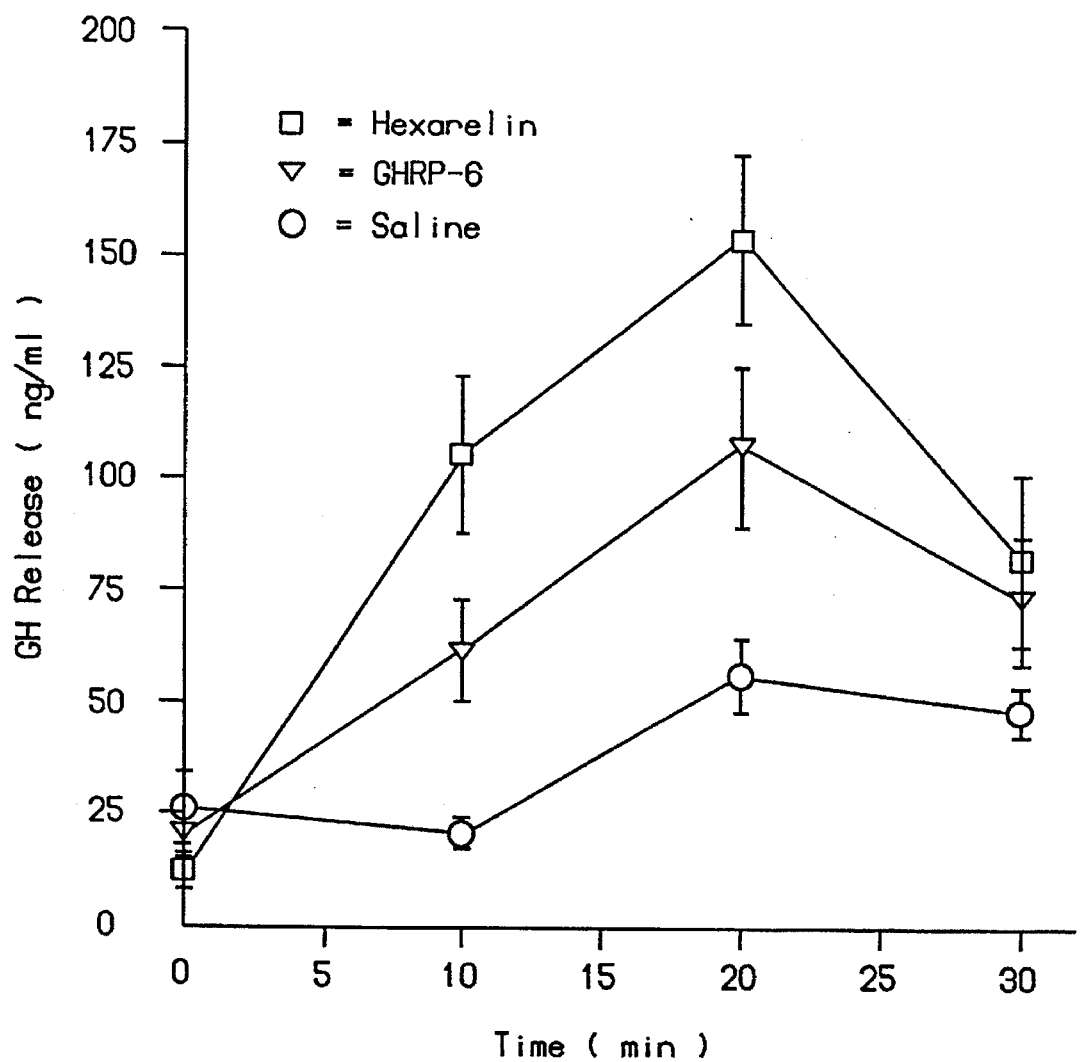
Figure 7:
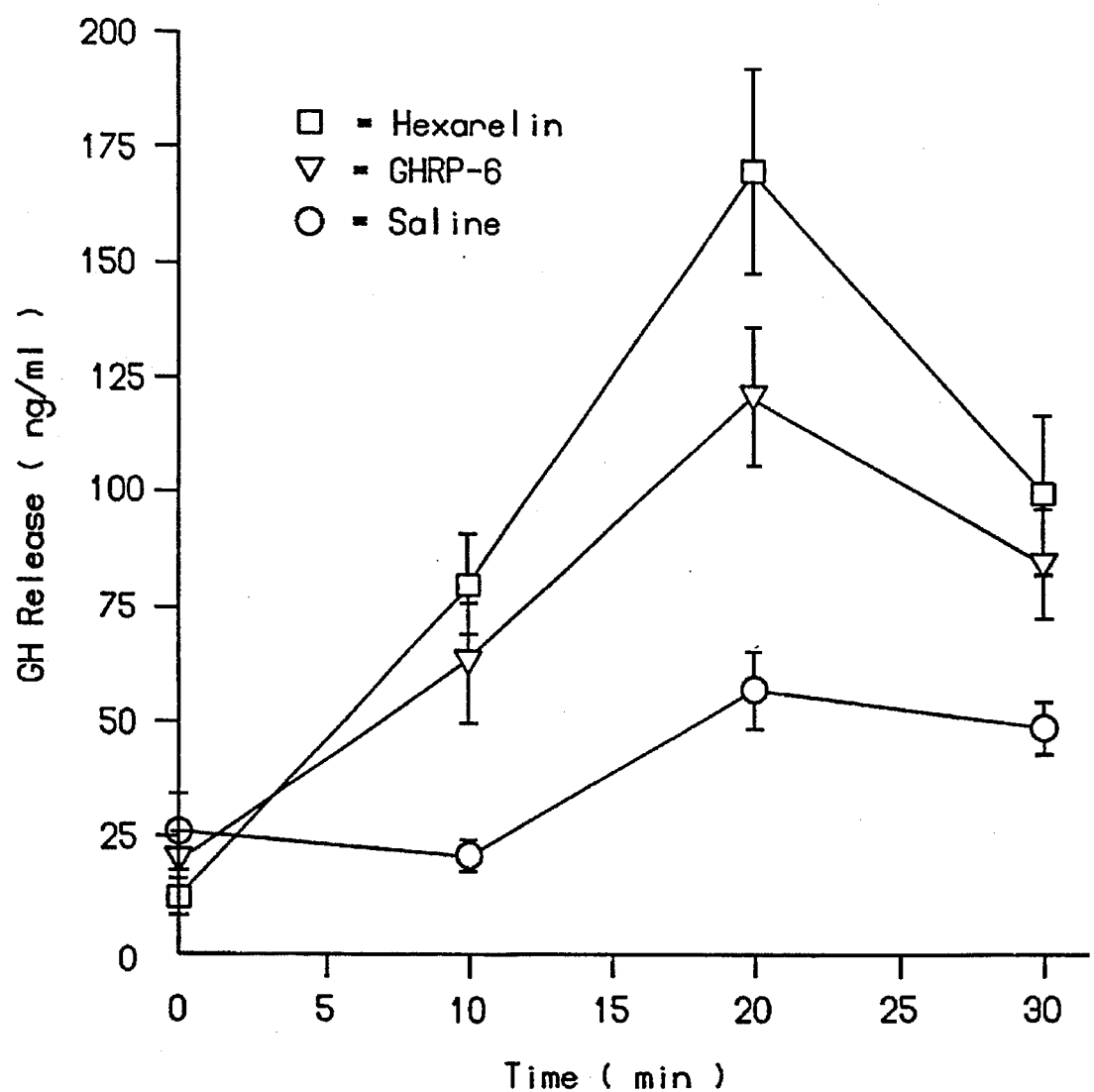
Figure 8:
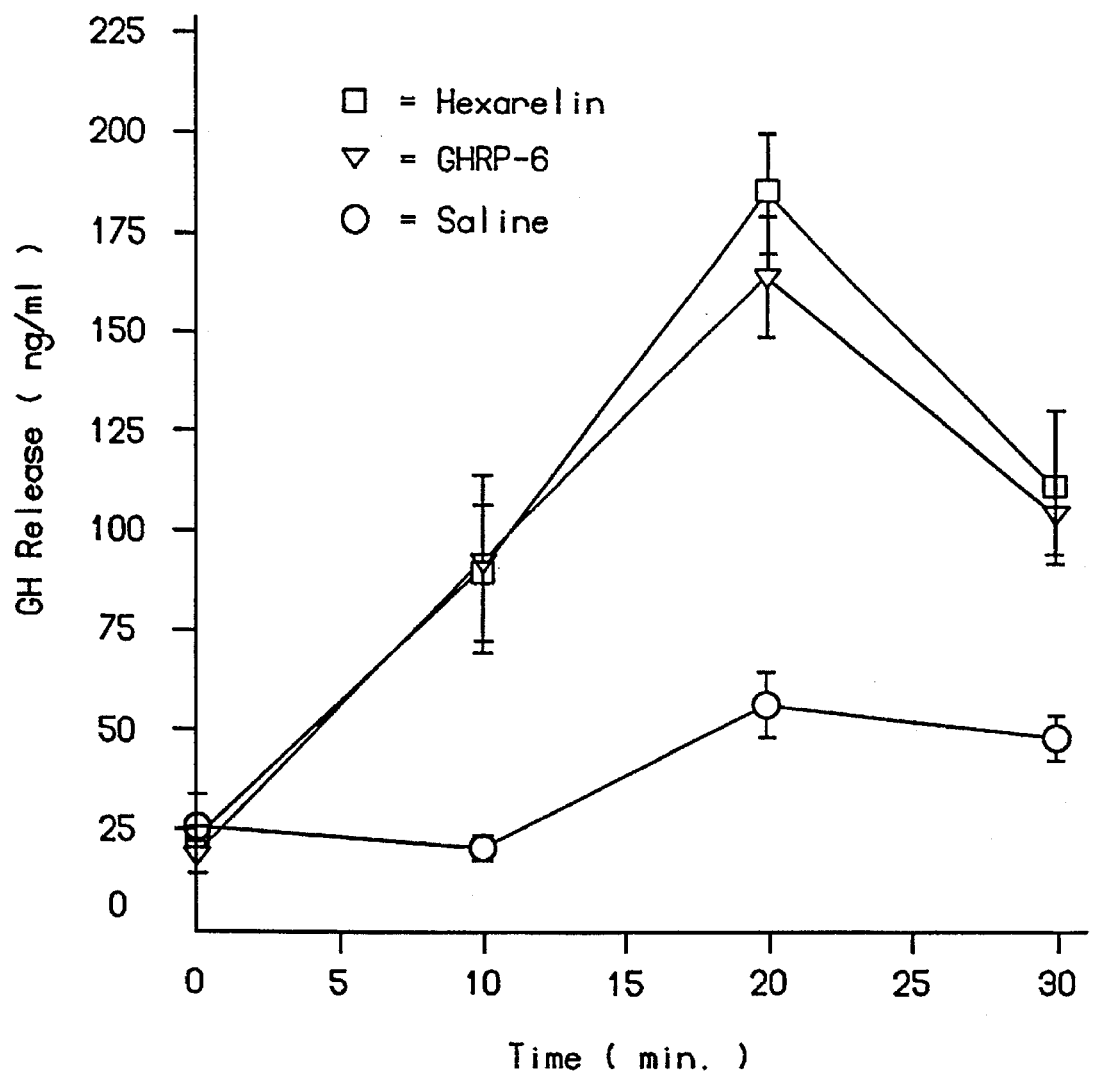

These data are also illustrated in FIGS. 6–8.

Example 11

Effect of HEXARELIN on GH Release in Pentobarbital-anesthetized Rats

Male Sprague Dawley rats weighing 225–250 g were divided in groups of five animals each. Rats were anesthetized with Nembutal injected intraperiteonally at 50 mg/kg, fifteen minutes prior to the first blood withdrawal taken over heparin by cardiac puncture (for determination of basal GH).

Subcutaneous injections of either HEXARELIN or GHRP-6 were given immediately after the first blood collection, and additional blood samples were collected 15 and 40 minutes later.

Measurement of rat GH was performed by a standard double antibody radioimmunoassay with reagents supplied by the National Pituitary Agency and the National Institute of Arthritis, Diabetes, and Digestive and Kidney Diseases. The standards used were NIADDK-NIH-rGH-RP-2. Statistical data were obtained with the Student's t Test at a significance level of 5%. Results are shown in Table 4.

TABLE 4

COMPARATIVE EFFECT OF GHRP-6 AND
HEXARELIN ON GH RELEASE IN
PENTOBARBITAL-ANESTHETIZED RATS
POST-DRUG PLASMA GH (ng/ml)

| COMPOUND | 0 min | 15 min | 40 min |
|---|---|---|---|
| Saline s.c. | 32 ± 15 | 43 ± 21 | 128 ± 38 |
| GHRP-6* s.c. | | | |
| 50 µg/kg | 57 ± 39 | 262 ± 58 | 97 ± 44 |
| 25 µg/kg | 41 ± 16 | 222 ± 95 | 110 ± 47 |
| HEXARELIN s.c. | | | |
| 50 µg/kg | 32 ± 16 | 439 ± 69** | 81 ± 13 |
| 25 µg/kg | 56 ± 21 | 388 ± 99* | 100 ± 51 |
| 10 µg/kg | 63 ± 58 | 95 ± 44 | 88 ± 29 |

Student's t test:
*1% P 5%
**0.1% P 1%
Statistical values obtained for HEXARELIN at 50 µg/kg and 25 µg/kg are compared to GHRP-6 at the same concentrations.

Figure 9:
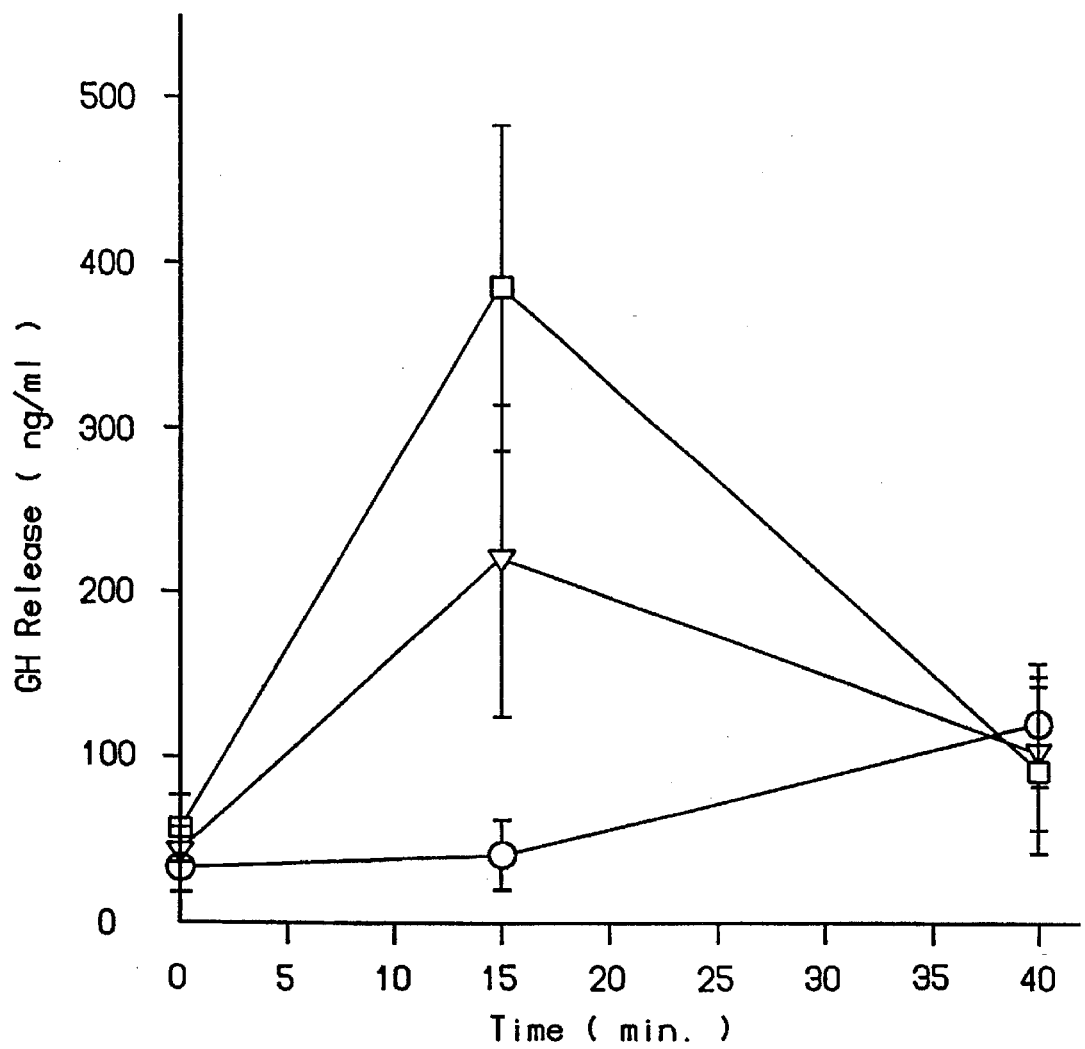
Figure 10:
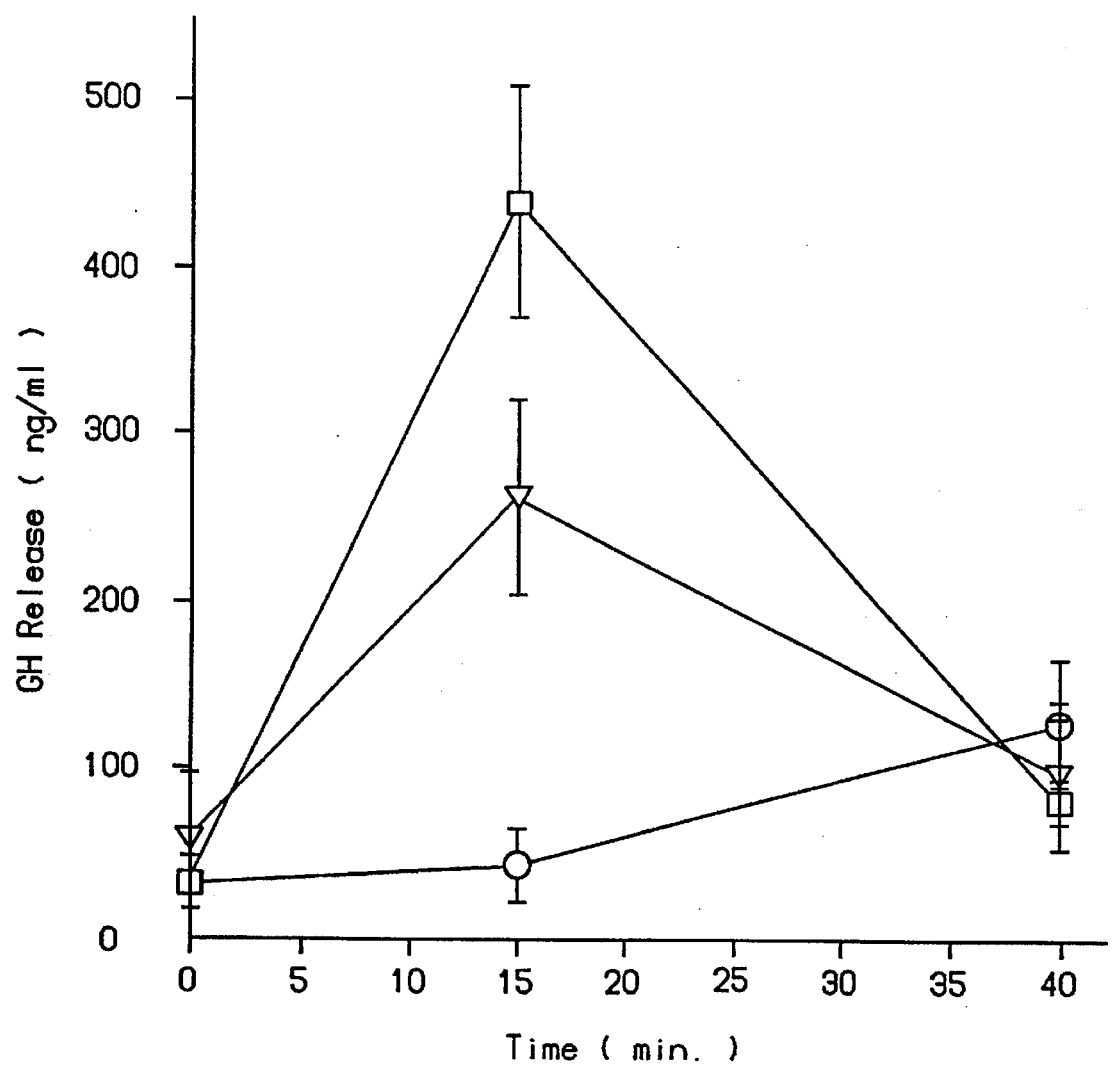
Figure 12:
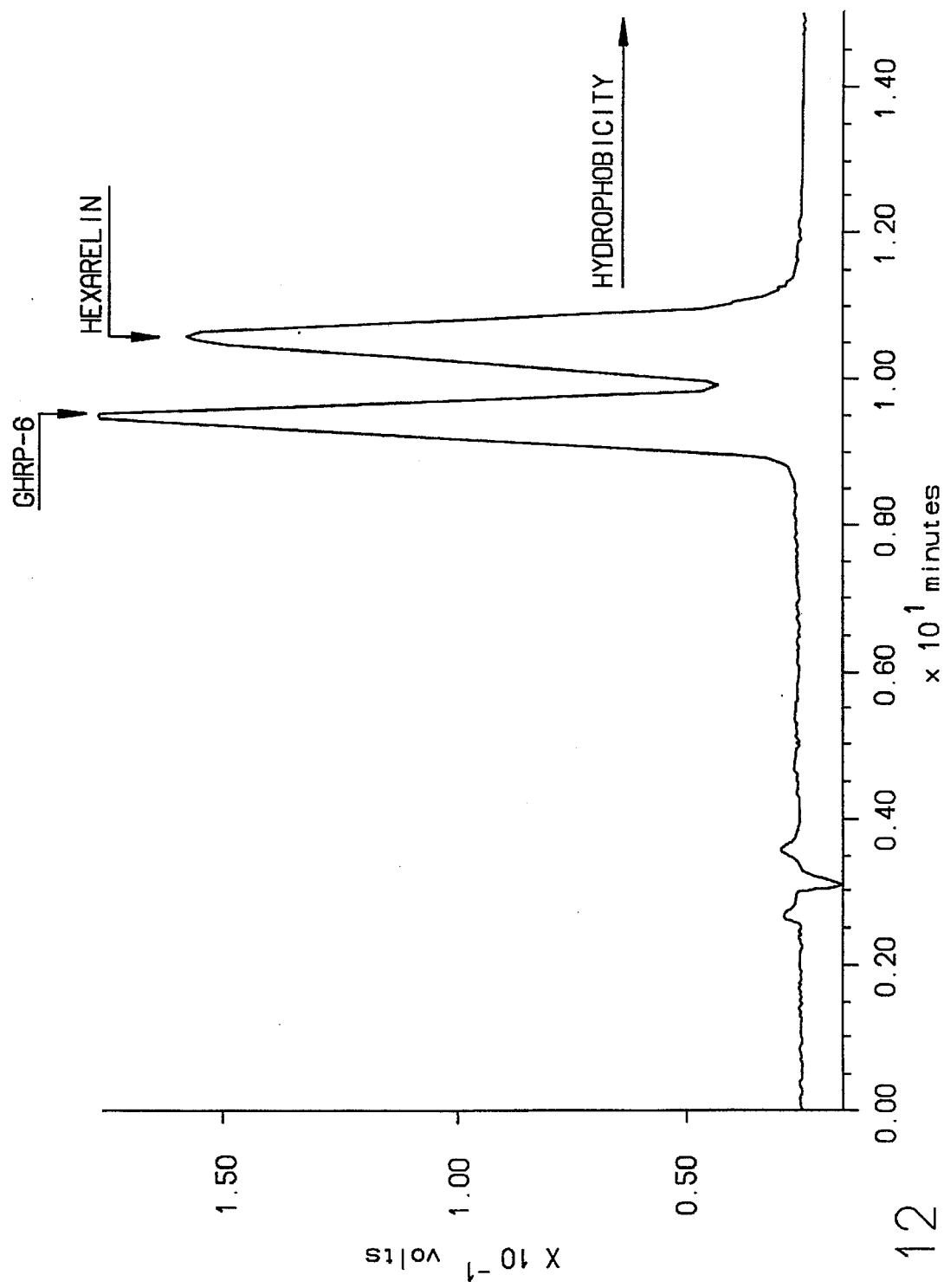
FIG. 12 is a graphical comparison of the hydrophobicity of GHRP-6 and HEXARELIN.

These data are also illustrated in FIGS. 9–11. Also, FIG. 12 illustrates that HEXARELIN has greater hydrophobicity than GHRP-6.

Example 12

These two peptides were also tested for acute cardiovascular toxicity in the rat.

HEXARELIN

| GROUP | DOSE (mg/Kg)(*) | NO. OF ANIMALS |
|---|---|---|
| 1 | 5 | 6 |
| 2 | 7.5 | 6 |
| 3 | 10 | 6 |

GHRP-6

| GROUP | DOSE (mg/Kg)($) | NO. OF ANIMALS |
|---|---|---|
| 4 | 2.5 | 6 |
| 5 | 5 | 6 |
| 6 | 7.5 | 6 |

(*)The dose levels of HEXARELIN were established by the Sponsor on the basis of a previous toxicity study.
($)The dose levels of GHRP-6 were established by the Sponsor on the basis of literature data (Macia R.A. et al., Toxicol. Appl. Pharm. 104, 403–410, 1990).

Dosages were calculated on the basis of the declared peptide content in each product, as specified below:
1) HEXARELIN: peptide content 79%
2) GHRP-6: peptide content 64%

A single dose of HEXARELIN or GHRP-6 was administered to rats in different calendar dates in such a way that each group/dose should be treated in two subsequent days.

Initially 3 rats/group/compound, the first ones in numerical order, were treated.

The treatment schedule was as follows:

| DAYS: | 1 | 2 | 3 | 4 | 5 | 6 |
|---|---|---|---|---|---|---|
| Groups | 3 and 4 | 3 and 4 | 1 and 5 | 1 and 5 | 2 and 6 | 2 and 6 |
| Cages | 5 and 7 | 6 and 8 | 1 and 9 | 2 and 10 | 3 and 11 | 4 and 12 |

For each compound, appropriate amounts of solutions in 0.9% NaCl for injection were prepared just before treatment at the suitable concentrations. The solutions were sterilized by filtration (Millipore filter, pore size 0.22 µm). Owing to the type of the study (acute study) in which formulates were administered just after preparation, stability checks were not performed. Concentration checks were also not performed. The volume of solution injected was maintained constant at 1 ml/Kg.

The intravenous injections were done as a single dose in one vein of the tail with an appropriately gauged sterile, disposable, plastic syringe. The injection rate was about 0.1 ml/sec.

Periodical observations were made up to 4 hours after treatment. Abnormality and mortality were recorded. Body weight was recorded once during pre-trial and on the administration day to calculate the volumes to be injected.

The mortality data obtained with the two products were:

| Dose | Dead rats/Total N° of rats per group |
|---|---|
| GHRP-6 | |
| 2.5 mg/kg | 0/6 |
| 5.0 mg/kg | 1/6 |
| 7.5 mg/kg | 2/6 |
| HEXARELIN | |
| 5.0 mg/kg | 0/6 |
| 7.5 mg/kg | 1/6 |
| 10 mg/kg | 2/6 |

The results indicate that HEXARELIN shows the same lethality as GHRP-6 but consistently at a higher dose, i.e., it is less toxic than GHRP-6, an unexpected finding particularly since HEXARELIN is more potent regarding its pharmacological activity.

Example 13

Stability of HEXARELIN Compared to GHRP6 after Irradiation in Solution

Solutions of Hexarelin and GHRP-6 in acetate buffer pH 5.4 (1 mg/ml w/v) were submitted to irradiation (Co 60) at doses varying from 0 to 1.6 MRad with intervals of 2 MRad.

Subsequently, the samples were analyzed by RP-HPLC using 27% Acetonitrile in water as solvent, and the area of the peptide peak was examined.

The figure shows the variation of the percentage of residual material according to the irradiation dose:

$$\left[ \frac{\text{Peak area for dose } X}{\text{Peak area of control}} \times 100 \right]$$

Figure 13:
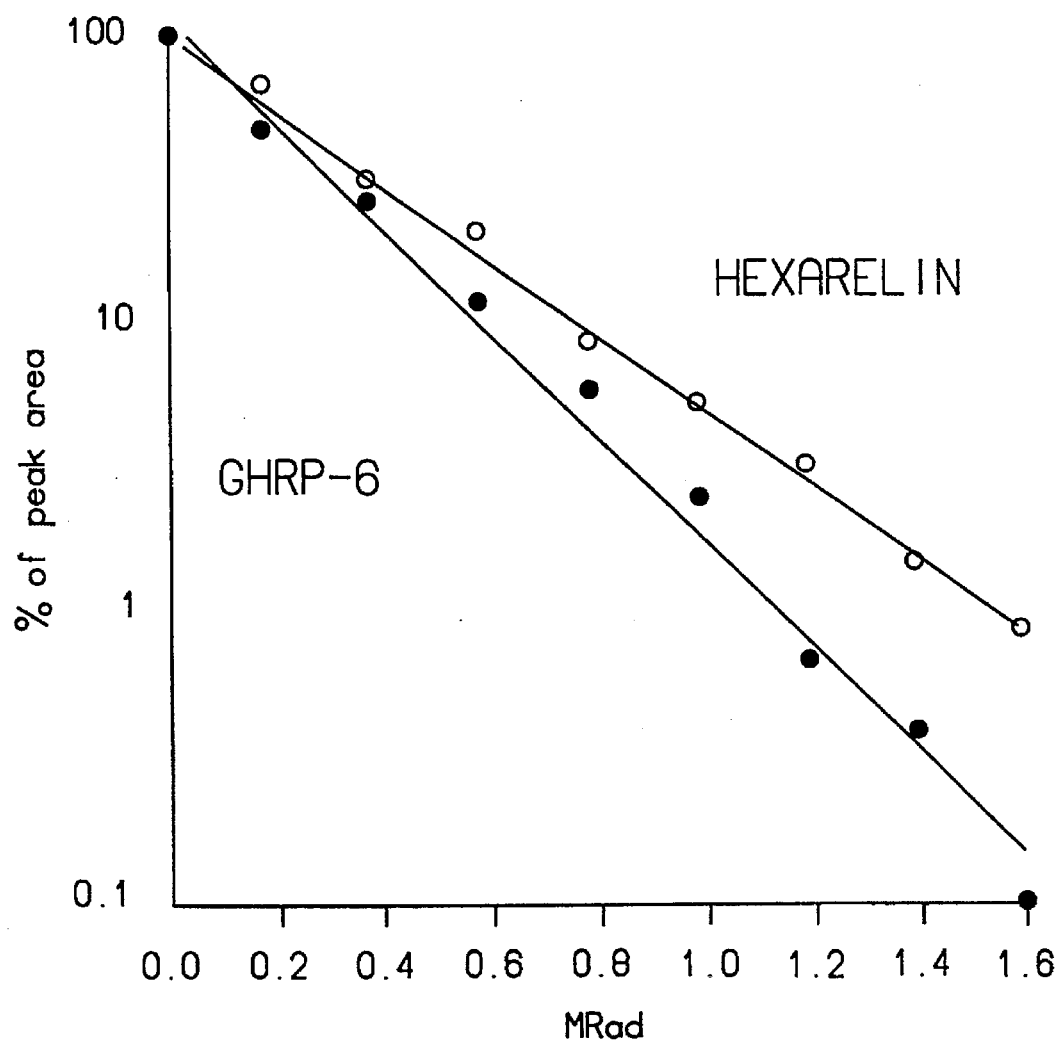
FIG. 13 is a graphical representation of the effect of irradiation on GHRP-6 and HEXARELIN in an acetate buffer solution.
Figure 14A:
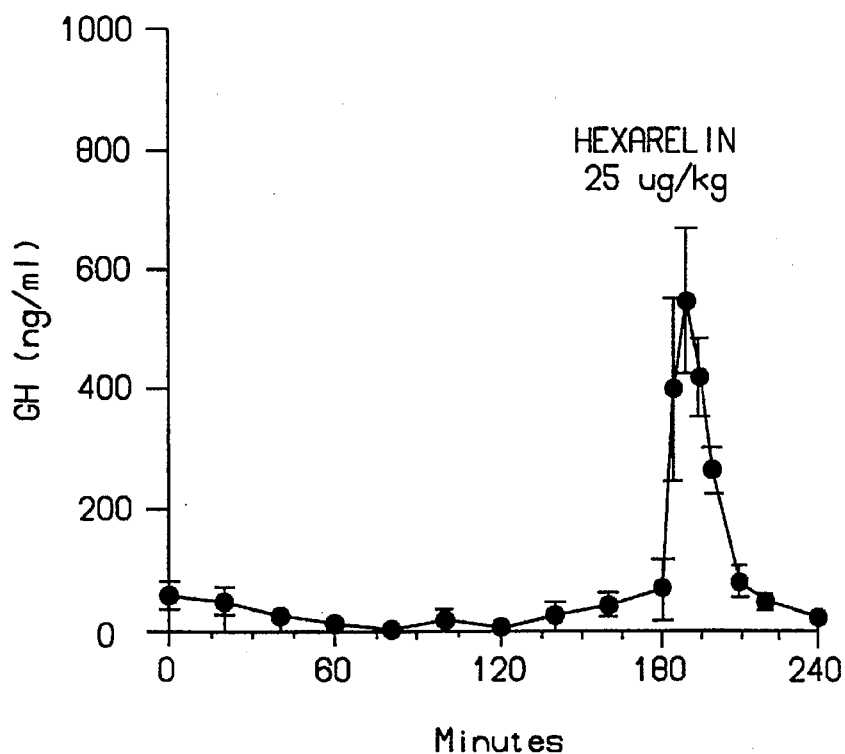
FIGS. 14A, 14B, 15A, 15B, 16A, 16B, 17A and 17B are graphical representations of GH release in anesthetized male rats following intravenous administration of saline, GHRP-6 and HEXARELIN.
Figure 14B:
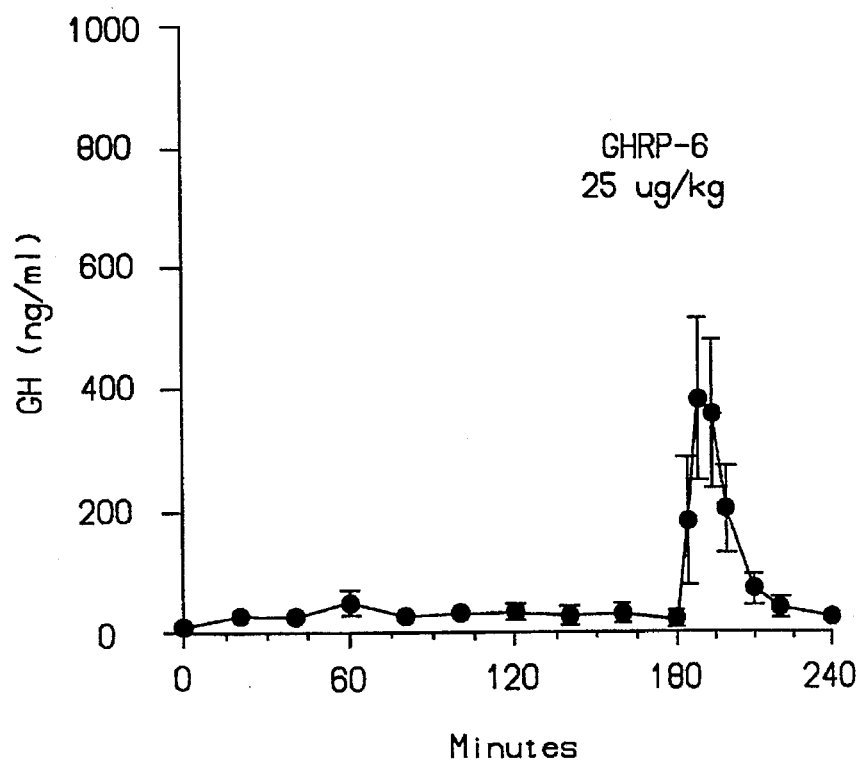
Figure 15A:
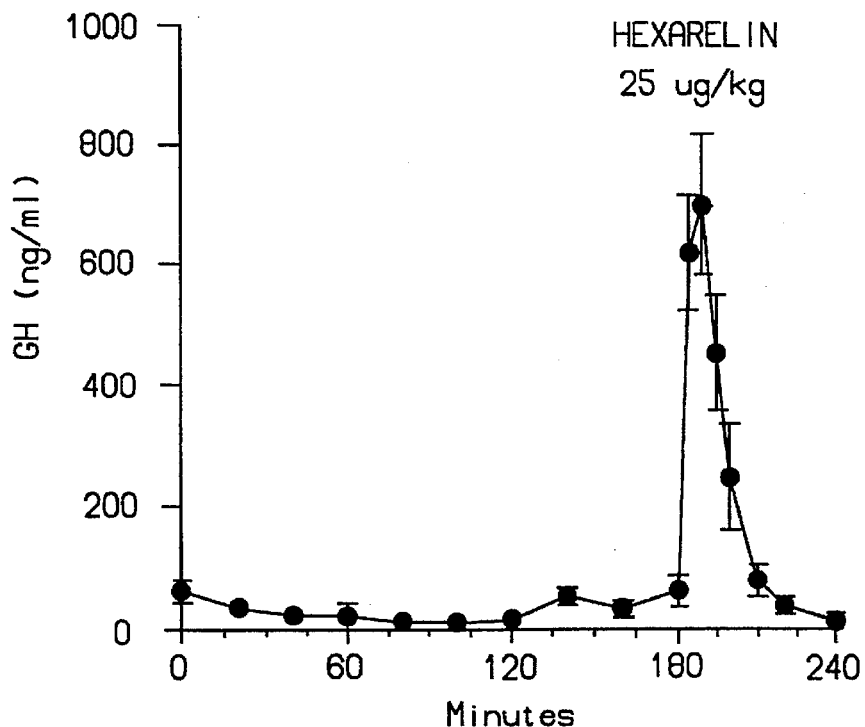
Figure 15B:
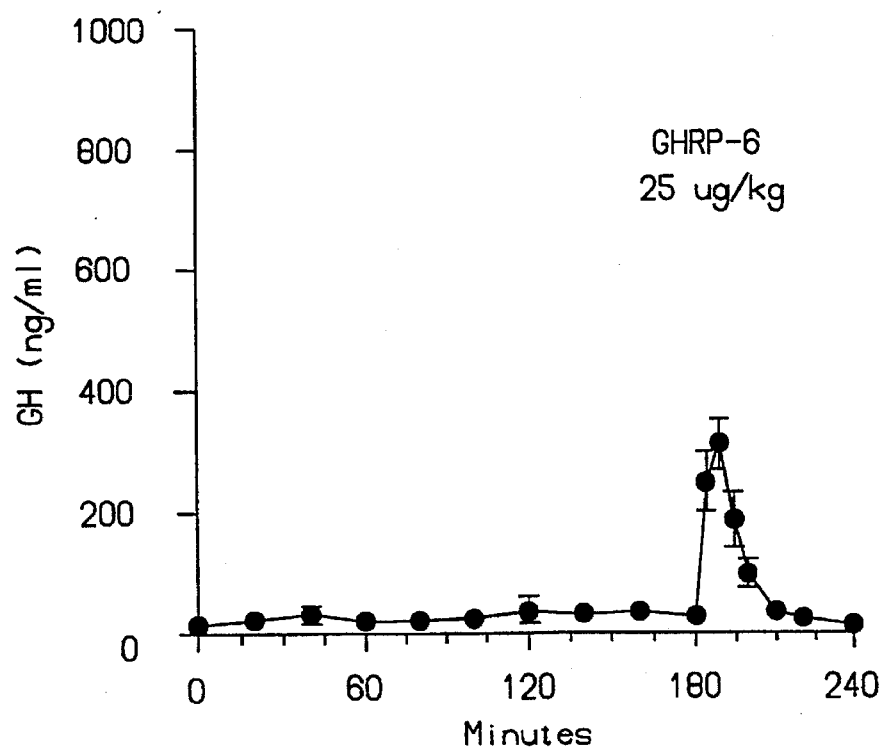
Figure 16A:
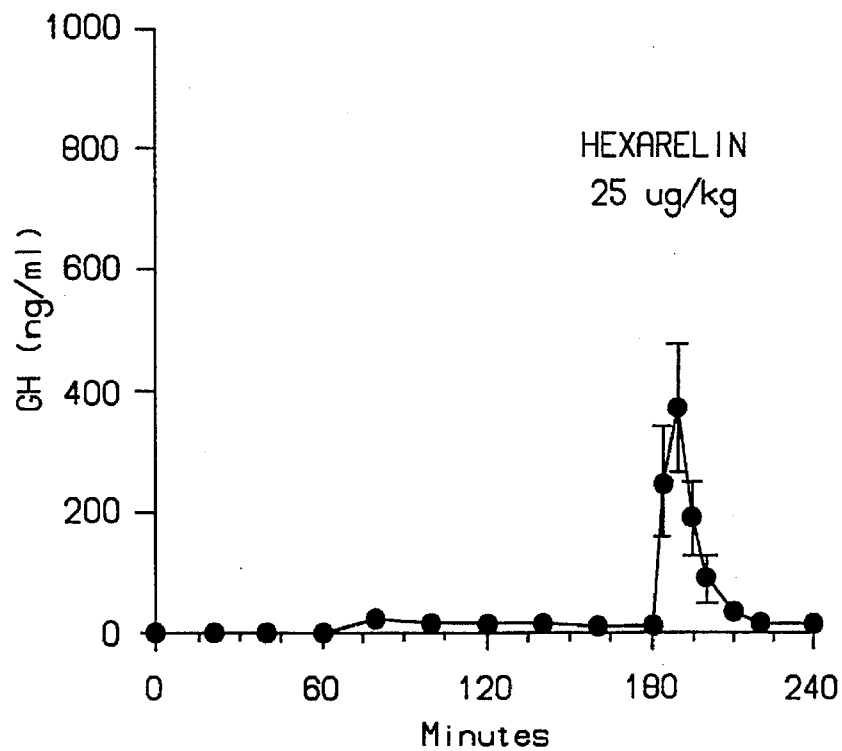
Figure 16B:
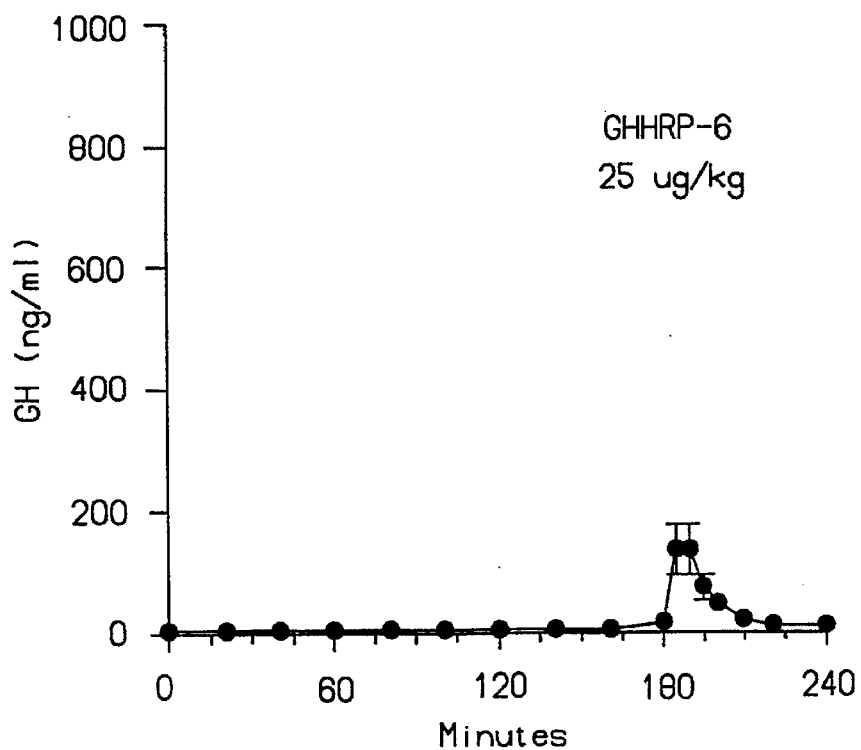
Figure 17A:
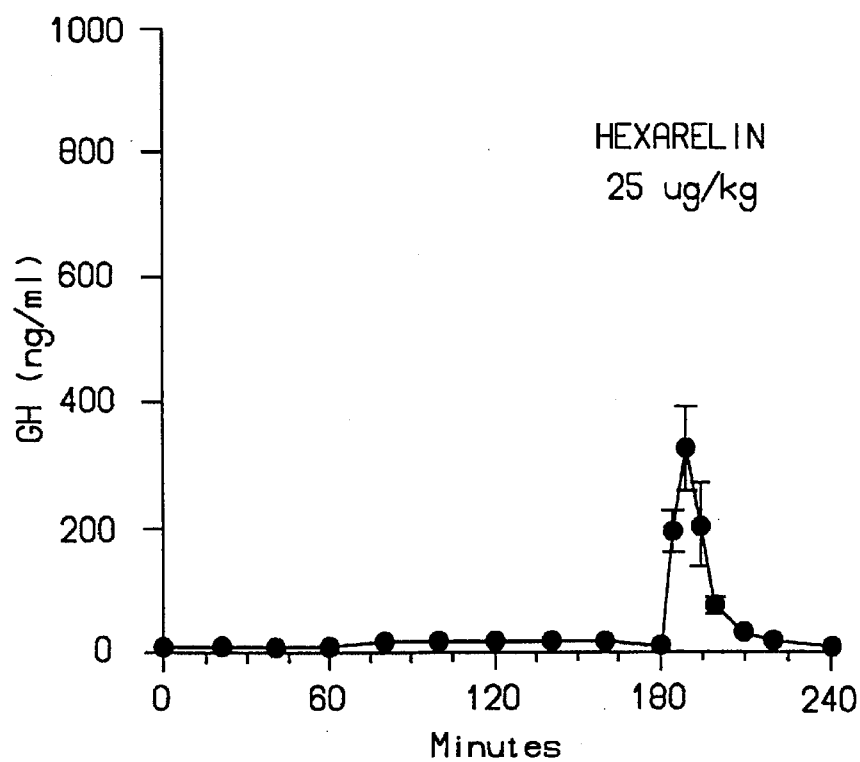
Figure 17B:
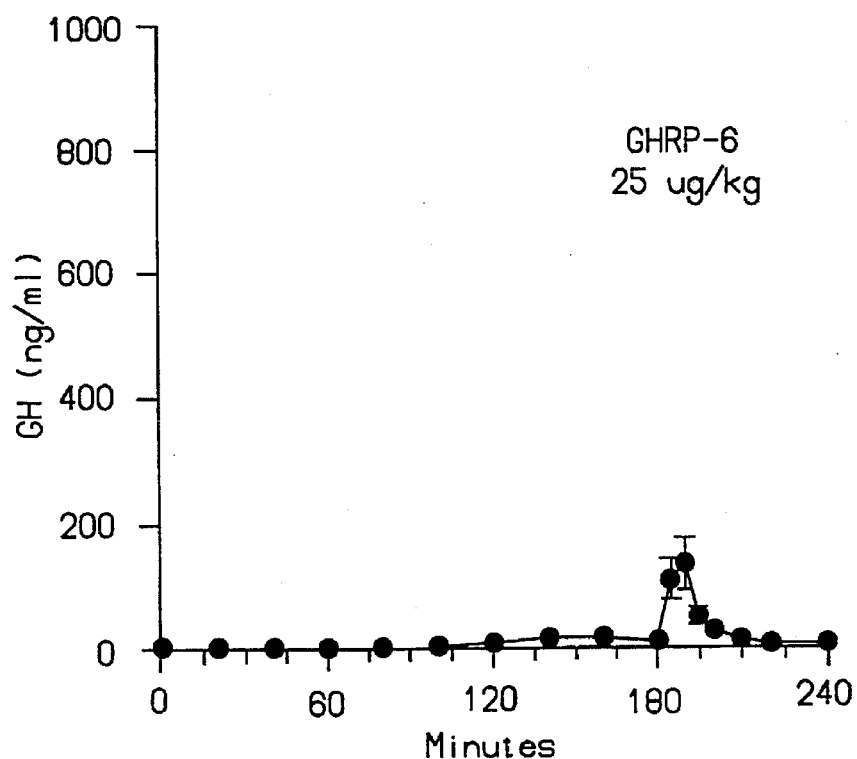
Figure 18:
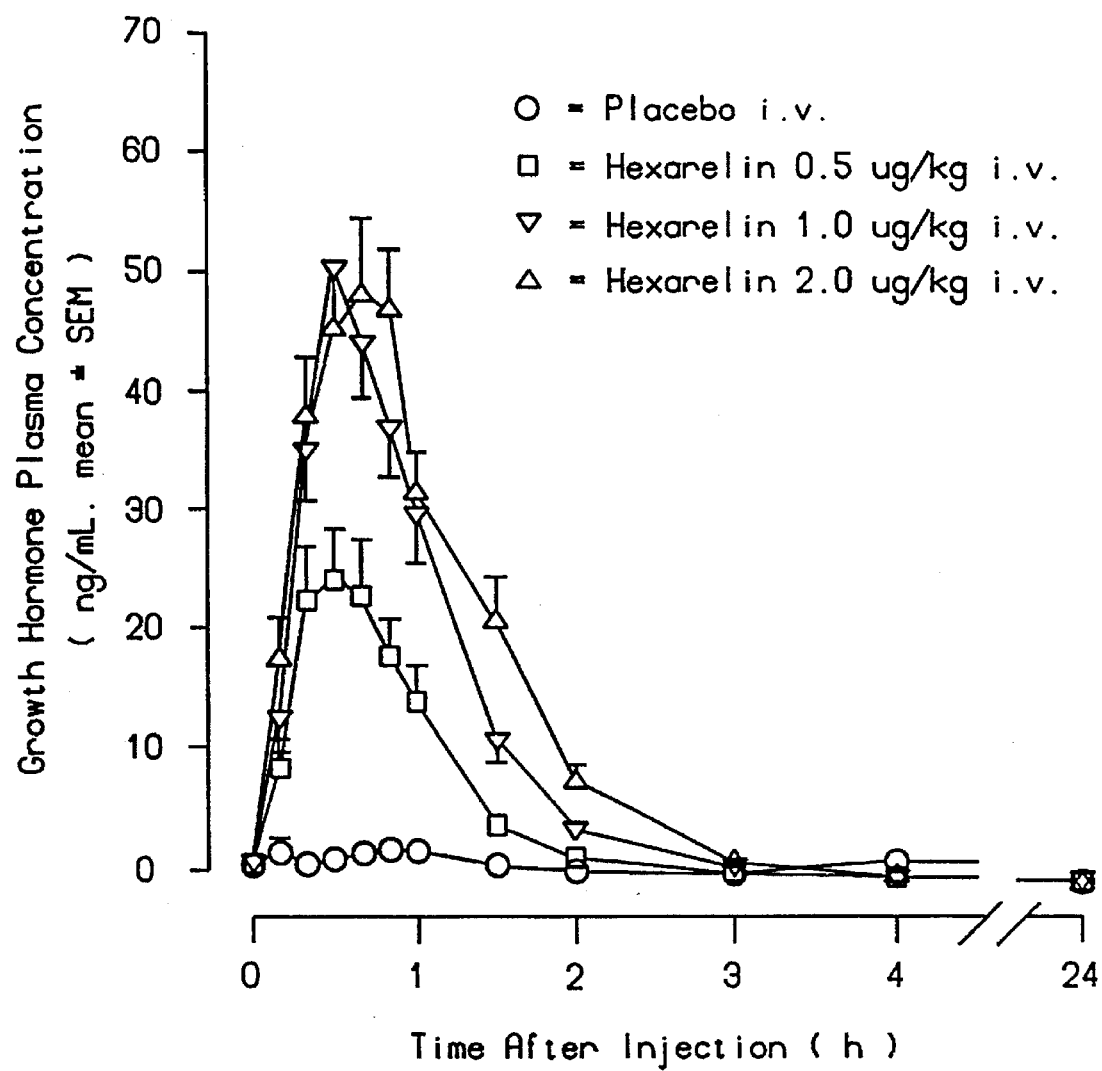
FIGS. 18, 19 and 20 are graphical representations of the effect of HEXARELIN on growth hormone secretion in young healthy male volunteers.
Figure 19:
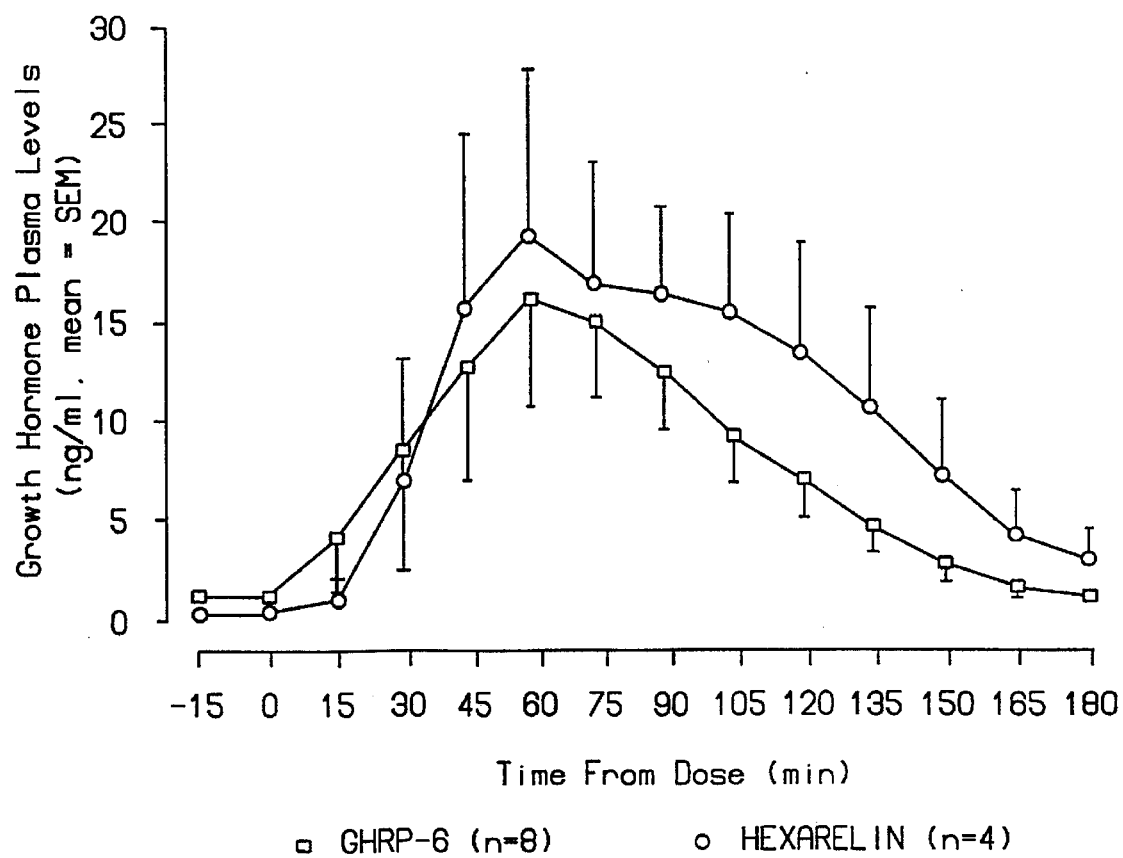

Results are shown in FIG. 13.

Example 14

In this example, the neuroendocrine mechanism by which HEXARELIN and GHRP-6 mediate their actions has been compared. Although previous studies have looked at the role of somatostatin in regulating the action of GHRP-6 in culture and in stressed animals, this study observes the role of both somatostatin and GHRH in regulating the action of HEXARELIN and GHRP-6 in conscious, freely-moving, nonstressed animals.

Sixty male rats were prepared with indwelling venous catheters under ether anesthesia three days before experimentation. On the day of experimentation, all animals were given an iv heparin injection (100 IU; 0630 h). At 0700 h, animals were treated with 0.5 ml of either normal serum (control-as), somatostatin antiserum (somatostatin-as; 0.25 ml+0.25 ml saline), growth hormone-releasing hormone antiserum (GHRH-as; 0.25 ml+0.25 ml saline), or both somatostatin antiserum and growth hormone-releasing hormone antiserum (0.25 ml somatostatin-as+0.25 ml GHRH-as). Blood sampling began 60 minutes after antiserum pretreatment, with blood samples collected every 20 minutes for three hours. After the 180 minute sample (1100 h), animals were treated iv with 25 µg/kg of either Hexarelin or GHRP-6. Blood samples were then collected at 5, 10, 15, 20, 30, 40, and 60 minutes after peptide treatment. All samples were centrifuged immediately and the plasma frozen until assayed. The peak GH response to Hexarelin and GHRP-6 as well as the area under the response curves (AUCs) for the thirty minutes following peptide injection were calculated. Data were subjected to repeated measures analysis of variance and are expressed as mean ±SEM.

Factorial analysis of variance identified several main treatment effects.

A. PEPTIDE EFFECTS: The pooled results obtained from treatment with either HEXARELIN or GHRP-6 suggest that, overall, HEXARELIN was more effective in eliciting a higher mean GH response as compared to GHRP-6, as shown in Table 5. GH AUC and peak GH responses were also significantly higher.

B. ANTISERA EFFECTS: Antisera pretreatment clearly demonstrated that GHRH antiserum inhibited the GH response to both Hexarelin and GHRP-6. The mean GH response was significantly inhibited in GHRH antiserum pretreated rats as compared to animals which were not pretreated (Table 6). The GH AUC and peak GH responses were significantly diminished.

TABLE 5

| | Main Treatment Effects | | |
|---|---|---|---|
| Peptides | Mean GH (ng/ml) | GH AUC (ng/ml/30 min) | Peak GH (ng/ml) |
| Hexarelin | 235 ± 21** | 7366 ± 912** | 552 ± 59** |
| GHRP-6 | 131 ± 13 | 4220 ± 665 | 293 ± 41 |
| Antiserum (as) | | | |
| control-as | 241 ± 31 | 7716 ± 1457 | 514 ± 97 |
| somatostatin-as | 224 ± 23 | 7011 ± 1003 | 516 ± 63 |
| GHRH-as | 116 ± 18" | 3771 ± 924" | 288 ± 69' |
| somatostatin-as + GHRH-as | 98 ± 14" | 3021 ± 565" | 249 ± 46' |

**($p < 0.01$) significantly higher than GHRP-6 treated animals.
' ($P < 0.01$), " ($P < 0.05$) significantly lower than control and somatostatin-as pretreated animals.

The responses of the individual treatment groups are also illustrated in FIGS. 15A, 15B, 16A, 16B, 17A, 17B, 18 and 19.

This Example investigated what role GHRH and somatostatin have in the neuroendocrine mechanism by which the GHRPs, HEXARELIN and GHRP-6, mediate their neuroendocrine effects. In vitro studies have suggested that the GHRPs exert an effect via a direct pituitary site of action. Here, however, the administration of HEXARELIN as well as GHRP-6 to conscious, freely-moving (non-stressed) animals, suggests that GHRH is integrally involved in the mechanism by which HEXARELIN and GHPR-6 mediate their GH-releasing effects in vivo. This corroborates an earlier study in acutely-treated, stressed animals where passive immunization of endogenous GHRH resulted in a diminished plasma GH diminished plasma GH response to GHRP-6.

It has previously been suggested that somatostatin is involved in the mechanism by which GHRP-6 mediates its neuroendocrine effects. This was an acute study, however, conducted in a fashion known to induce stress, and thus, increase somatostatin tone in rats. In contrast, the results of the present study suggest minimal somatostatin involvement. We find these results surprising, both in light of the previous study and since we have found somatostatin to be involved in most GH-releasing mechanisms previously examined. The apparent disparity in results between the two studies may be accounted for by the fact that we performed our study in non-stressed, conscious, freely-moving rats. In such non-stressed animals, somatostatin tone is variable: low during a GH peak, or high may underestimate the importance of somatostatin in this mechanism. For these reasons, we are hesitant to exclude the involvement of somatostatin at this time and feel that further analysis of somatostatin's involvement is warranted.

Example 15

Figure 20:
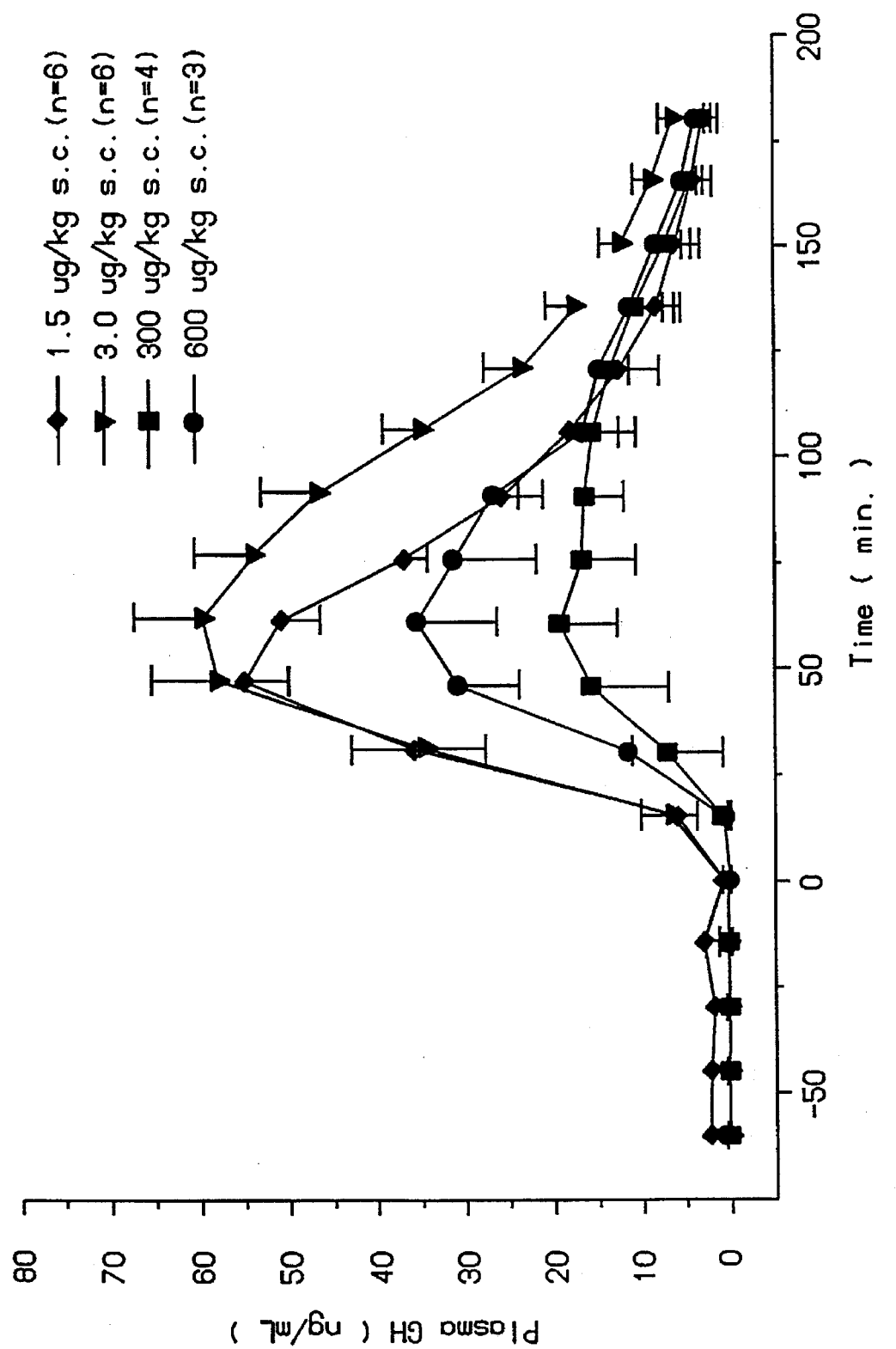

The effects of HEXARELIN on growth hormone secretion in young (20–30 years old) healthy male volunteers were measured after the administration of various dosages. The results shown in FIGS. 18–20 demonstrate that the peptide is effective in vivo as well as in vitro.

Example 16

The peptide of Example 3 was formulated in a polymeric PLGA implant in the form of rods which were about 1 cm long and 1 mm in diameter. These implants contained a loading of either 20 or 25% of the peptide (an amount of 7 or 10 mg), and were inserted subcutaneously into in male Beagle dogs which weighed between 10 and 12 kg. After an initial flare-up, plasma testosterone fell below castration levels after approximately 10 days, and was maintained for approximately 180 days. The absence of response after a stimulation by i.v. administration of the peptide at day 145 indicates down-regulation of the pituitary receptors. No clinical side effects were observed during this study.

Although the aforementioned examples of the present invention disclose specific embodiments thereof, it is believed that the substitution of an D-2-alkylTryptophan in bioactive peptides which contain at least one Tryptophan residue will yield bioactive peptides providing the advantages and benefits discussed above.

The incorporation of a D-2-alkylTryptophan in bioactive peptides as described above provides a method for prolonging and preserving the activity of such peptides. When analogous bioactive peptides not substituted with an D-2-alkylTryptophan are exposed to various processing conditions and substances, the activity of such peptides may be adversely effected. Sterilizing procedures used in the pharmaceutical industry may expose bioactive compounds to ionizing radiation. Such radiation may effect the formation of reactive radicals. Tryptophan containing peptides are particularly susceptible to attack by such radicals and such attack may render the peptide ineffective, or possibly toxic.

Furthermore, various formulating compounds, such as polylactic-polyglycolic acid (PLGA) polymers may contain active, or activated groups which may also attack Tryptophan containing bioactive peptides. The present invention provides a method for protecting a tryptophan containing bioactive peptide from these manufacturing hazards while also increasing the peptides resistance to oxidative degradation after formulation is complete. It is believed that the presence of the alkyl group at the number 2 position of the Tryptophan increases the stability of the pyrrole ring wherein attack by reactive radicals and active or activated groups occurs.

While it is apparent that the invention herein disclosed is well calculated to fulfill the objects above stated, it will be appreciated that numerous embodiments and modification may be devised by those skilled in the art, and it is intended that the appended claims cover all such modification and embodiments as fall within the true spirit and scope of the present invention.

What is claimed is:

1. A method for preparing D-2-alkyl Tryptophan which comprises:

treating a solution of racemic N$^{\alpha}$-acetyl-2-alkyl Tryptophan with acylase and a base;

retaining the solution for about 24 hours at about 40° C. to form insoluble material therein;

recovering and lyophilizing the insoluble material to form a residue;

dissolving the residue in a solvent;

subjecting the solvent and dissolved residue to chromatography to obtain highly polar fractions and lesser polar fractions;

collecting the lesser polar fractions to obtain a $N^{\alpha}$-acetyl-D-2-alkyl Tryptophan compound; and hydrolyzing the $N^{\alpha}$-acetyl-D-2-alkyl-Tryptophan compound under an inert gas with a base for about 24 hours at 100° F., prior to the addition of an acid and cooling of the solution to obtain D-2-alkyl Tryptophan.

2. The method of claim 1 wherein the insoluble fraction is obtained by filtration, the residue is formed by lyophilizing the insoluble material to dryness, the residue is then dissolved in the upper phase of n-BuOH-AcOH-$H_2O$, and the chromatography step is conducted in a column.

3. A method for preparing D-2-alkyl Tryptophan which comprises:

treating a $N^{\alpha}$-acetyl-D-2-alkyl Tryptophan compound under an inert gas with a base for a sufficient time and at a sufficient temperature to hydrolyze said compound and form a solution;

adding an acid to the solution; and cooling the resultant solution to form D-2-alkyl Tryptophan.

4. The method of claim 3 wherein the resultant D-2-alkyl Tryptophan is purified by being filtered, washed, dried and recrystallized from hot water.

5. The method of claim 3 wherein the $N^{\alpha}$-acetyl-D-2-alkyl-Tryptophan compound is prepared by treating a solution of racemic $N^{\alpha}$-acetyl-2-alkyl Tryptophan with acylase for a sufficient time and at a sufficient temperature to form insoluble material therein;

recovering and lyophilizing the insoluble material to form a residue;

dissolving the residue in a solvent;

subjecting the solvent and dissolved residue to chromatography to obtain highly polar fractions and lesser polar fractions; and collecting the lesser polar fractions to obtain the $N^{\alpha}$-acetyl-D-2-alkyl-Tryptophan compound.

6. The method of claim 5 wherein the racemic $N^{\alpha}$-acetyl-2-alkyl-Tryptophan is dissolved in water with a base prior to treatment by the acylase, and the resulting solution is retained at about 40° C. for about 24 hours.

7. The method of claim 3 wherein the hydrolyzing treatment is conducted under an inert gas for about 24 hours at about 100° F.

8. The method of claim 3 wherein the acid is acetic acid and the solution is cooled for about 12 hours prior to recovering the D-2-alkyl Tryptophan.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: Xaa is pyro- glutamate ( x i ) SEQUENCE DESCRIPTION: SEQ ID NO:1:

```
Xaa  His  Trp  Ser  Tyr  Trp  Leu  Arg  Pro  Gly
1              5                        1 0
```